United States Patent
Drain

(10) Patent No.: US 11,628,017 B1
(45) Date of Patent: Apr. 18, 2023

(54) SURGICAL INSTRUMENT WITH LED LIGHTING AND ABSOLUTE ORIENTATION

(71) Applicant: Prichard Medical, LLC, Rocky River, OH (US)

(72) Inventor: Joseph Prichard Drain, Rocky River, OH (US)

(73) Assignee: Prichard Medical, Inc., Rocky River, OH (US)

( * ) Notice: Subject to any disclaimer, the term of this patent is extended or adjusted under 35 U.S.C. 154(b) by 0 days.

(21) Appl. No.: 17/510,950

(22) Filed: Oct. 26, 2021

Related U.S. Application Data

(63) Continuation of application No. PCT/US2020/029882, filed on Apr. 24, 2020, which is a continuation of application No. 16/395,986, filed on Apr. 26, 2019, now abandoned, which is a continuation-in-part of application No. 15/619,747, filed on Jun. 12, 2017, now abandoned.

(60) Provisional application No. 62/413,355, filed on Oct. 26, 2016.

(51) Int. Cl.
  *A61B 34/20* (2016.01)
  *A61B 17/16* (2006.01)
  *A61B 90/30* (2016.01)

(52) U.S. Cl.
  CPC .............. *A61B 34/20* (2016.02); *A61B 17/16* (2013.01); *A61B 90/30* (2016.02); *A61B 2034/2048* (2016.02); *A61B 2034/2051* (2016.02); *A61B 2090/309* (2016.02)

(58) Field of Classification Search
  CPC ..................... A61B 34/20; A61B 90/30; A61B 2090/309; A61B 2034/2048; A61B 90/35; A61B 2034/2046
  See application file for complete search history.

(56) References Cited

U.S. PATENT DOCUMENTS

| | | | |
|---|---|---|---|
| 5,953,683 A | 9/1999 | Hansen et al. |
| 7,559,931 B2 | 7/2009 | Stone |
| 8,057,482 B2 | 11/2011 | Stone et al. |
| 8,118,815 B2 | 2/2012 | Van der Walt |
| 8,241,296 B2 | 8/2012 | Wasielewski |
| 8,740,810 B2 | 6/2014 | Sanbuichi |
| 8,814,877 B2 | 8/2014 | Wasielewski |

(Continued)

FOREIGN PATENT DOCUMENTS

| | | |
|---|---|---|
| EP | 1635705 B1 | 1/2012 |
| WO | WO 2009/055034 A1 | 4/2009 |
| WO | WO 2013/169674 A1 | 11/2013 |

OTHER PUBLICATIONS

International Search Report dated Aug. 3, 2020 for Int'l Patent App. No. PCT/US2020/029882, filed Apr. 24, 2020.

(Continued)

*Primary Examiner* — Diane D Yabut
*Assistant Examiner* — Christina C Lauer
(74) *Attorney, Agent, or Firm* — BakerHostetler

(57) ABSTRACT

A surgical instrument having a position sensor that may be detachable, disposable, partially isolated from movement of the main body of the surgical instrument, and/or configured to display feedback lighting. The orientation of the surgical instrument may be mimicked either virtually or by a mechanical device with a second surgical instrument. The instruments of the present disclosure may be used in any procedure or treatment that would benefit from position feedback for the instruments.

18 Claims, 19 Drawing Sheets

(56) References Cited

U.S. PATENT DOCUMENTS

| | | |
|---|---|---|
| 9,532,730 B2 | 1/2017 | Wasielewski |
| 9,795,451 B2 | 10/2017 | Gorek et al. |
| 2009/0318836 A1 | 12/2009 | Stone et al. |
| 2010/0076505 A1 | 3/2010 | Borja |
| 2010/0125172 A1 | 5/2010 | Jayaraj |
| 2010/0137869 A1 | 6/2010 | Borja et al. |
| 2011/0208093 A1 | 8/2011 | Gross et al. |
| 2011/0313281 A1* | 12/2011 | Grinberg ............ A61B 17/1633 600/424 |
| 2012/0319859 A1 | 12/2012 | Taub et al. |
| 2013/0303845 A1 | 11/2013 | Skula et al. |
| 2014/0030669 A1 | 1/2014 | Hey et al. |
| 2014/0052149 A1 | 2/2014 | Van der Walt et al. |
| 2015/0119637 A1 | 4/2015 | Alvarez et al. |
| 2015/0127009 A1 | 5/2015 | Berend et al. |
| 2015/0238204 A1 | 8/2015 | Stone |
| 2015/0272696 A1 | 10/2015 | Fry et al. |
| 2015/0305786 A1 | 10/2015 | Wehrle et al. |
| 2015/0366714 A1 | 12/2015 | Kandavel et al. |
| 2016/0242934 A1 | 8/2016 | Van det Walt et al. |
| 2016/0310077 A1 | 10/2016 | Hunter et al. |
| 2016/0354162 A1 | 12/2016 | Yen et al. |
| 2017/0172458 A1* | 6/2017 | Kato ...................... A61B 5/067 |
| 2018/0058536 A1* | 3/2018 | Pathak .................... G05B 5/01 |
| 2018/0110569 A1 | 4/2018 | Drain |
| 2018/0193171 A1 | 7/2018 | Van der Walt et al. |

OTHER PUBLICATIONS

Written Opinion dated Aug. 3, 2020 for Int'l Patent App. No. PCT/US2020/029882, filed Apr. 24, 2020.

Bosch Sensortec; BNO055 Intelligent 9-Axis Absolute Orientation Sensor Data Sheet; Document Revision 1.4; Release Date, Jun. 2016; Document No. BST-BNO055-DS000-14.

* cited by examiner

SURGICAL INSTRUMENT WITH LED LIGHTING AND ABSOLUTE ORIENTATION

RELATED APPLICATIONS

This application is a continuation of International Application No. PCT/US2020/029882, filed Apr. 24, 2020, which is a continuation of U.S. Non-Provisional application Ser. No. 16/395,986 filed on Apr. 26, 2019, which is a continuation-in-part of U.S. Non-Provisional application Ser. No. 15/619,747 filed on Jun. 12, 2017, which claims the benefit of U.S. Provisional Application No. 62/413,355 filed on Oct. 26, 2016, the contents of each of which are incorporated herein by reference in their entirety.

FIELD OF INVENTION

The disclosure relates generally to surgical and medical instruments. More particularly, this disclosure relates to surgical and medical instruments having high intensity lighting and absolute orientation sensors. The instruments of the present disclosure may be used in any suitable procedure or treatment which would benefit from high intensity lighting of the area to be treated or of interest, as well as knowing the orientation of such instrument in three-dimensional space. While reference is made herein to surgical instruments in particular, it should be understood that this disclosure is directed to medical, dental, or other instruments used in the treatment of humans or animals requiring lighting and absolute orientation knowledge.

BACKGROUND

Adequate lighting of an area to be treated is of great importance for any surgical or medical procedure. Operating room lighting may allow a surgeon to have an improved view of the surgical field. In this regard, lighting arrays may be provided in operating rooms or outpatient clinics to assist in illuminating the surgical field. Alternatively, bulky fiber-optic cable can also be used to illuminate the surgical field by being placed in or near the surgical field. Additional light emitters, such as headlamps and the like, worn by medical personnel may also be employed. However, in all these instances the light emitter is generally provided some distance away from the surgical instrument, and/or away from the surgical field, and/or in an orientation not conducive to illuminating critical portions of the surgical instrument or the surgical area. As such, the surgical instrument and light emitters are separated and shadows may be cast on the surgical field by the user, the electrosurgical instrument, or other obstructions (e.g., table drapes, other devices utilized during surgery, user's hand, etc.).

In addition, determining the optimal or desired alignment and/or orientation of surgical or medical instruments, such as for the proper placement of implants into the body, and maintaining such alignment and/or orientation as required for the selected procedure has long been a challenge. The surgeon must be provided with efficient and reliable feedback as to the orientation of the instrument in three-dimensional space with respect to the patient's body or treatment area in order to quickly and accurately correct any errors or issues with the orientation. Failure to do so may cause damage to the patient. Orientation data can be exploited in multiple settings, several of which occur in the operating room: hand-held, powered, or robotic surgical instruments all stand to benefit from real-time calculation of their precise orientation, location, as well as their linear and angular acceleration and velocity.

As example of this application outside of the operating room, doctors regularly perform a biopsy procedure involving the insertion of a biopsy needle into an object to be examined (e.g., a living body such as a human body) and extracting a tissue sample from a biopsy region in the object. Generally, in order to reduce the physical burden on patient, it is desirable to insert the biopsy needle near the biopsy region to reliably and accurately extract a tissue sample from the biopsy region. Accordingly, it has been customary in a biopsy to carry out a stereoscopic image capturing process in which radiation is applied to an object to be examined, and a stereoscopic image of the object is acquired, and then to calculate a three-dimensional position of the biopsy region from the stereoscopic image, before the biopsy procedure begins.

However, even if the three-dimensional position of the biopsy region is accurately mapped in advance of the procedure, it is possible that the needle may deviate from the desired puncture path (e.g., an interference with a blood vessel in the object). As a result, the inserted biopsy needle does not follow the desired puncture path, and then the positional relationship, i.e., distance and direction relationship, between the biopsy region from which a tissue sample is to be extracted and the opening of the biopsy needle. To solve the problem, there have been proposed various technologies for aspirating and sampling an appropriate amount of tissue from a biopsy region through a biopsy needle without the need for inserting the biopsy needle again. This is just another manner in which this technology can be deployed in the medical setting.

There is a need for surgical and medical instruments to include a high intensity light source and/or absolute orientation sensors to improve the effectiveness of such instruments

SUMMARY

The following presents a simplified overview of the example embodiments in order to provide a basic understanding of some aspects of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented later.

In accordance with embodiments herein, the present disclosure is directed to surgical and medical instruments and devices having absolute orientation sensors and/or high intensity lighting. The instruments of the present disclosure may be used in any suitable procedure or treatment which would benefit from knowing the orientation of the surgical instrument or high intensity lighting of the area to be treated or of interest. While reference is made herein to surgical instruments in particular, it should be understood that this disclosure is directed to medical, dental, or other instruments used in the treatment of humans or animals requiring lighting and absolute orientation. Absolute orientation means that the absolute orientation sensors may not require calibration against a known point or plane in order to provide orientation related information. The absolute orientation sensor may comprise an accelerometer, gyroscope, and magnetometer, and may be able to generate an absolute orientation by using the Earth itself as a reference point or plane, by sensing the Earth's magnetic field, and by extension, the Earth's magnetic core, rather than an arbitrarily determined point or plane.

According to one aspect of the invention, a surgical instrument comprises an instrument body, an absolute orientation sensor including an absolute orientation sensing component, the absolute orientation sensor being configured to be attached to the instrument body such that when the absolute orientation sensor is attached to the instrument body the absolute orientation sensing component would be at least partially fixed relative to the instrument body. When the absolute orientation sensing component is at least partially fixed relative to the instrument body the absolute orientation sensing component would be operable to detect a plurality of orientation data associated with at least one orientation condition of the surgical instrument relative to the Earth's magnetic field without requiring calibration by a separate arbitrary reference plane, the absolute orientation sensor being at least partially detachable from the instrument body such that the absolute orientation sensing component is removable from the instrument body, where when the absolute orientation sensing component is removed the absolute orientation sensing component would not be operable to detect the plurality of orientation data associated with the at least one orientation condition of the surgical instrument.

According to another aspect of the invention, a surgical instrument comprises an instrument body, an absolute orientation sensor including an absolute orientation sensing component, the absolute orientation sensor being configured to be attached to the instrument body such that when the absolute orientation sensor is attached to the instrument body the absolute orientation sensing component would be partially fixed relative to the instrument body. When the absolute orientation sensing component is at least partially fixed relative to the instrument body the absolute orientation sensing component would be operable to detect a plurality of orientation data associated with at least one orientation condition of the surgical instrument relative to the Earth's magnetic field without requiring calibration by a separate arbitrary reference plane, the absolute orientation sensor being configured to partially isolate movement of the instrument body from absolute orientation sensing component when the absolute orientation sensor is attached to the instrument body, where when the absolute orientation sensing component is partially fixed relative to the instrument body the instrument body would be partially movable relative to the absolute orientation sensing component.

According to another aspect of the invention, a surgical instrument comprises a device processor operable for controlling one or more components of the surgical instrument, at least one light source operatively coupled to the device processor and controlled in part by the device processor, the device processor being configured to operate the light source based on the orientation of the surgical instrument.

Features of any of the above aspects may be combined with one another. For example, a surgical instrument may include a detachable absolute orientation sensor that is partially fixable relative to an instrument body and the surgical instrument may provide feedback (e.g., light feedback) based on the orientation sensed by the absolute orientation sensor. Any of the surgical instruments may include the at least one light source to operate the at least one light source based on the orientation of such surgical instrument. In any of the embodiments, the orientation sensor may not be an absolute orientation sensor. For example, the orientation sensor may be a relative orientation sensor that includes a relative orientation sensing component instead of or in addition to an absolute orientation sensing component.

One embodiment may be a surgical instrument comprising: a device processor operable for controlling one or more components of the surgical instrument; an absolute orientation sensing component operatively coupled to the device processor and controlled in part by the device processor, wherein the absolute orientation sensing component may comprise an accelerometer, gyroscope, and magnetometer, wherein the absolute orientation sensing component may be operable to detect a plurality of orientation data associated with at least one orientation condition of the surgical instrument relative to the Earth's magnetic field without requiring calibration by a separate arbitrary reference plane, and generate a plurality of orientation status data on at least a portion of the plurality of detected orientation data; and at least one power source operatively coupled to the absolute orientation sensing component, wherein the at least one power source may be operable to generate a supply of power for operation of the device processor and the absolute orientation sensing component. The surgical instrument may further comprise a display operatively coupled to the device processor, wherein the display may be operable to display at least a portion of the plurality of generated orientation status data thereon. The plurality of orientation data may comprise at least one from the group consisting of a location data, pitch data, roll data, and yaw data. The location data may comprise x, y, and z coordinate values. The plurality of orientation data may further comprise at least one selected from the group consisting of angular velocity data, acceleration data, magnetic field strength data, linear acceleration data, gravity data, and temperature data. The surgical instrument may further comprise an input/output device operably coupled to the device processor and controlled in part by the device processor; wherein the input/out device may be operable to transmit at least a portion of the plurality of generated orientation status data to a remote device. The surgical instrument may further comprise an audio component operatively coupled to the device processor and controlled in part by the device processor, wherein the device processor may be further operable to generate at least one audio response based in response to at least a portion of the plurality of generated orientation status data for output by the audio component. The surgical instrument may further comprise at least one light source operatively coupled to the device processor and controlled in part by the device processor, wherein the at least one light source may be located on the surgical instrument such that the at least one light source may be operable to direct light towards a specified area on an associated patient. The at least one light source may be a high lumen light source. The at least one light source may be a light emitting diode, compact fluorescent, incandescent, fluorescent, or halogen bulb. The device processor may be operable to activate the at least one light source when the surgical device is in use. The surgical instrument may be drills, drivers, saws, wire insertion devices, burr, awls, scalpels, suction, retraction devices, mallets, biopsy needles, unpowered drills, unpowered drivers, unpowered saws, unpowered wire inserters, and unpowered burrs. Additionally, the surgical instrument may be a robotic surgical device, such as robotic arms or other assisted medical devices which provide a user or robot with real-time orientation data.

Another embodiment may be a surgical instrument comprising a device processor operable for controlling one or more components of the surgical instrument; an absolute orientation sensing component operatively coupled to the device processor and controlled in part by the device processor, wherein the absolute orientation sensing component may comprise an accelerometer, gyroscope, and magnetometer, wherein the absolute orientation sensing component may be operable to detect a plurality of orientation data associated with at least one orientation condition of the surgical instrument relative to the Earth's magnetic field without requiring calibration by a separate arbitrary reference plane, and generate a plurality of orientation status data on at least a portion of the plurality of detected orientation data; at least one power source operatively coupled to the absolute orientation sensing component, wherein the at least one power source may be operable to generate a supply of power for operation of the device processor and the absolute orientation sensing component; and an audio component operatively coupled to the device processor and controlled in part by the device processor, wherein the device processor may be further operable to generate at least one audio response based in response to at least a portion of the plurality of generated orientation status data for output by the audio component; wherein the plurality of orientation data may comprise at least one from the group consisting of a location data, pitch data, roll data, and yaw data, angular velocity data, acceleration data, magnetic field strength data, linear acceleration data, gravity data, and temperature data; and wherein the location data may comprise x, y, and z coordinate values. The surgical instrument may further comprise an input/output device operably coupled to the device processor and controlled in part by the device processor; wherein the input/out device may be operable to transmit at least a portion of the plurality of generated orientation status data to a remote device. The surgical instrument may further comprise a display operatively coupled to the device processor, wherein the display may be operable to display at least a portion of the plurality of generated orientation status data thereon. The surgical instrument may further comprise at least one light source operatively coupled to the device processor and controlled in part by the device processor, wherein the at least one light source may be located on the surgical instrument such that the at least one light source may be operable to direct light towards a specified area on an associated patient; wherein the light source may be a high lumen light source; wherein the light source may be a light emitting diode, compact fluorescent, incandescent, fluorescent, or halogen bulb; wherein the device processor may be operable to activate the light source when the surgical device may be in use.

Another embodiment of the surgical instrument may comprise: a device processor operable for controlling one or more components of the surgical instrument; at least one light source operatively coupled to the device processor and controlled in part by the device processor, wherein the at least one light source may be located on the surgical instrument such that the at least one light source may be operable to direct light towards a specified area on an associated patient; wherein the light source may be a high lumen light source; wherein the light source may be a light emitting diode, compact fluorescent, incandescent, fluorescent, or halogen bulb; wherein the device processor may be operable to activate the light source when the surgical device may be in use; and at least one power source operatively coupled to the light source, wherein the at least one power source may be operable to generate a supply of power for operation of the device processor and the light source. The surgical instrument may further comprise an absolute orientation sensing component operatively coupled to the device processor and controlled in part by the device processor, wherein the absolute orientation sensing component may comprise an accelerometer, gyroscope, and magnetometer, wherein the absolute orientation sensing component may be operable to detect a plurality of orientation data associated with at least one orientation condition of the surgical instrument relative to the Earth's magnetic field without requiring calibration by a separate arbitrary reference plane, and generate a plurality of orientation status data on at least a portion of the plurality of detected orientation data; and further comprising an audio component operatively coupled to the device processor and controlled in part by the device processor, wherein the device processor may be further operable to generate at least one audio response based in response to at least a portion of the plurality of generated orientation status data for output by the audio component; wherein the plurality of orientation data may comprise at least one from the group consisting of a location data, pitch data, roll data, and yaw data, angular velocity data, acceleration data, magnetic field strength data, linear acceleration data, gravity data, and temperature data; and wherein the location data may comprise x, y, and z coordinate values. The surgical instrument may further comprise an input/output device operably coupled to the device processor and controlled in part by the device processor; wherein the input/out device may be operable to transmit at least a portion of the plurality of generated orientation status data to a remote device. The surgical instrument may further comprise a display operatively coupled to the device processor, wherein the display may be operable to display at least a portion of the plurality of generated orientation status data thereon.

Still other advantages, aspects and features of the subject disclosure will become readily apparent to those skilled in the art from the following description wherein there is shown and described a preferred embodiment of the present disclosure, simply by way of illustration of one of the best modes best suited to carry out the subject disclosure As it will be realized, the present disclosure is capable of other different embodiments and its several details are capable of modifications in various obvious aspects all without departing from the scope herein. Accordingly, the drawings and descriptions will be regarded as illustrative in nature and not as restrictive.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

DETAILED DESCRIPTION

Figure 1:
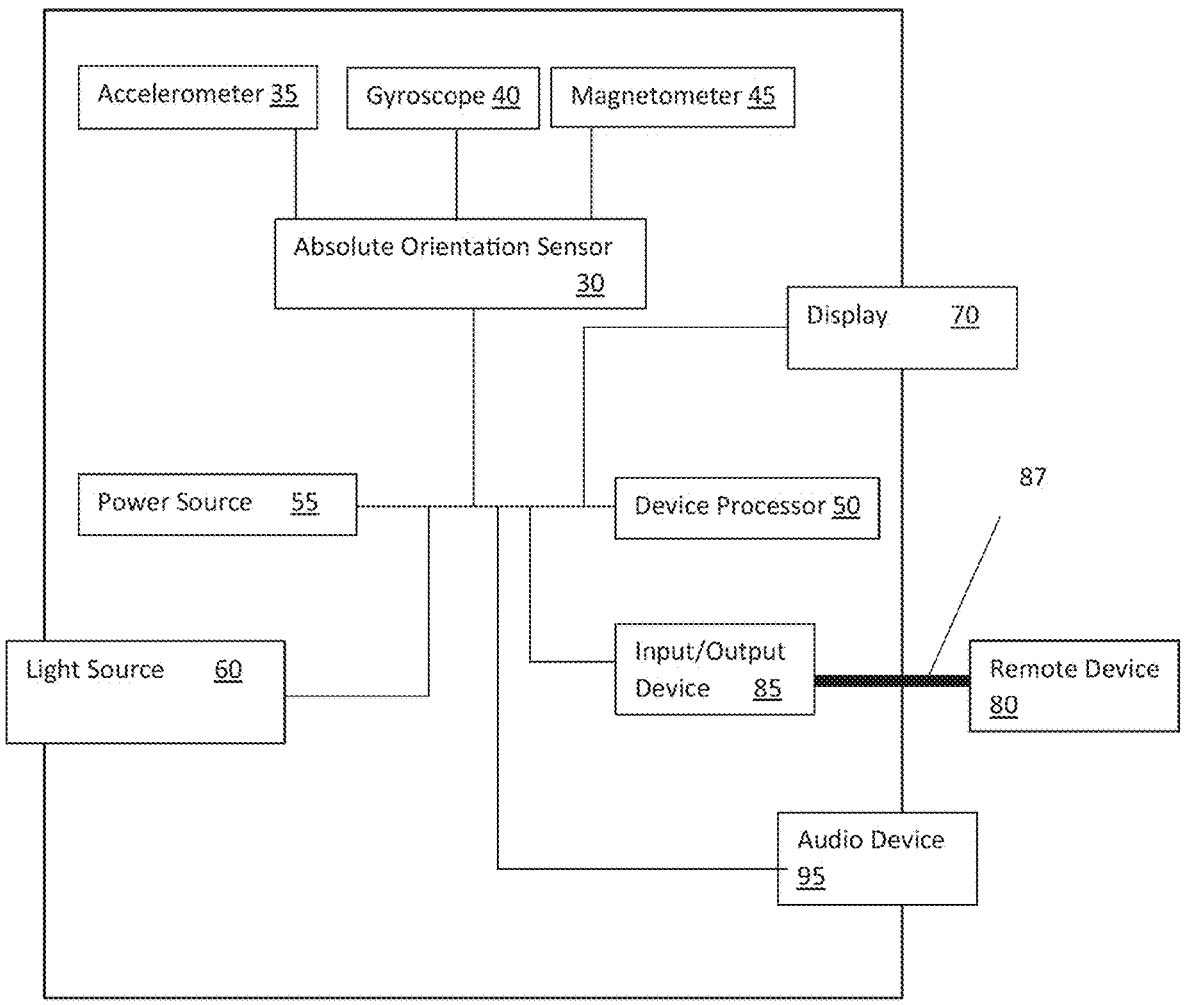
FIG. 1 is a block diagram of a surgical instrument.
Figure 1:
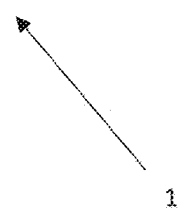

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present in all embodiments described herein.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware embodiments. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, may be implemented by special purpose hardware-based computer systems that perform the specified functions or steps, or combinations of special purpose hardware and computer instructions.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 0.001-10% from the indicated number or range of numbers.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

The absolute orientation sensor may comprise an accelerometer, gyroscope, and magnetometer, and may be able to generate an absolute orientation by using the Earth itself as a reference point or plane, by sensing the Earth's magnetic field, and by extension, the Earth's magnetic core, rather than an arbitrarily determined point or plane. When the absolute orientation sensor is connected to a surgical instrument the orientation of the absolute orientation sensor may be extrapolated to determine the orientation of the surgical instrument. This orientation of the surgical instrument may be conveyed to a user through display on a digital display that is located on the surgical instrument, or the orientation information may be transmitted to an external electronic device. The absolute orientation sensor may be attachable to substantially any surgical device. Additionally, the surgical instrument may have a high lumen light source to assist a user in viewing a place of a body to be operated upon.

The accompanying drawings incorporated herein and forming a part of the specification illustrate the example embodiments.

FIG. 1 is a block diagram of a surgical instrument. As shown in FIG. 1, the surgical instrument 1 may comprise an absolute orientation sensor 30, accelerometer 35, gyroscope 40, magnetometer 45, device processor 50, power source 55, light source 60, display 70, input/output device 85, remote device 80, communication link 87, and audio device 95.

The accelerometer 35, gyroscope 40, and magnetometer 45 may be components of the absolute orientation sensor 30. An accelerometer measures linear acceleration, such that an accelerometer at rest on the surface of the Earth measures a positive acceleration of 9.81 m/s, and an accelerometer in free fall towards the center of the Earth measures an acceleration of 0 m/s. A gyroscope, historically is a spinning wheel or disc in which the axis of rotation is free to assume any orientation by itself but in this instance a microelectrical mechanical system, is useful for measuring or maintaining orientation, providing information about angular acceleration, velocity, and position. The combination of an accelerometer and a gyroscope are often included in inertial navigation systems. A magnetometer is an instrument that measures magnetism-either magnetization of magnetic material like a ferromagnet, or the direction, strength, or the relative change of a magnetic field at a particular location.

The power source 55 may provide power to the absolute orientation sensor 30, device processor 50, light source 60, display 70, input/output device 85, and audio device 95. The device processor 50 may be operatively coupled to, and control, the absolute orientation sensor 30, device processor 50, light source 60, display 70, input/output device 85, and audio device 95.

The device processor 50 may be, or may comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The device processor 50 may be coupled (e.g., communicatively, operatively, etc.) to auxiliary devices or modules of the surgical instrument 1 using a bus or other coupling.

The absolute orientation sensor 30 may capture, in real-time, various orientation variables of the surgical instrument 1, including location, pitch, roll, yaw angular acceleration, velocity, and position; linear acceleration, velocity, and position, as well as magnetic field strength, linear acceleration, gravity, and/or temperature. Location may include x, y, and z coordinate values, and other indicators of position in three-dimensional space.

The absolute orientation sensor 30 may be configured to generate orientation information that is particular to the tool being used. For example, when the absolute orientation sensor 30 is on the surgical instrument 1, particularly important orientation information may include information relating to location, pitch, roll, and yaw of the tip or active portion of the surgical instrument 1, such as a drill portion of an awl, or other manual, powered, hand held, robotic or other surgical device or tool. The absolute orientation sensor 30 may also be calibrated such that the orientation information generated by the absolute orientation sensor 30 is directly readable on the tip or active portion of the surgical instrument 1 by calculating the differences in orientation of the absolute orientation sensor 30 and tip or active portion of the surgical instrument 1 during a calibration step. Importantly, while it may be recommended to calibrate the absolute orientation sensor 30 relative to the tip or active portion of the surgical instrument 1, it is not required that the absolute orientation sensor 30 be calibrated against an arbitrary point or plane. The combination of accelerometer 35, gyroscope 40, and magnetometer 45 allow the absolute orientation sensor 30 to self-calibrate by using the Earth's magnetic field and/or the Earth's core as reference points or planes. In one embodiment, the absolute orientation sensor 30 may comprise a microelectricalmechanical system (MEMS) multi-axis gyroscope, multi-axis accelerometer, and a multiaxial geomagnetic sensor that is able to generate output information comprising quaternion, Euler angles, rotation vector, linear acceleration, gravity, and heading. A combination of multiaxis gyroscope, multiaxis accelerometers, and multiaxis geomagnetic sensors (magnetometer) may comprise an Inertial Measurement Unit mode.

In one embodiment, the absolute orientation sensor 30 may comprise an accelerometer 35 that outputs absolute orientation in the "X", "Y", and "Z" axis as well as angular velocity, acceleration, magnetic field strength, linear acceleration, gravity, and temperature. "X" and "Y" orientation of the instrument may output onto a display, providing the user an absolute value of where the surgical instrument is held in space. The addition of the gyroscope 40 may allow the absolute orientation sensor 30 to measure tilt, rotation, and changes in angular momentum. The addition of the magnetometer 45 allows for the measurement of the magnetic field of the Earth and the Earth's core. The combination of the accelerometer 35, gyroscope 40, and magnetometer 45 allows the absolute orientation sensor 30 to calibrate itself against a fixed point, the Earth's core, and thereby be accurate regardless of where the absolute orientation sensor 30 is in use.

This may allow the user to move the surgical instrument and receive real time quantified feedback about the angle and orientation of the surgical instrument. This may aid in surgical instrument alignment and its use, in one instance the placement of screws. The absolute orientation sensor 30 comprise any suitable sensors and related components for determining orientation as is known in the art. Examples include, but are not limited to, accelerometers 35, gyroscopes 40, magnetometers 45, and the like, and combinations thereof. The absolute orientation sensor 30 may interface wirelessly or wired, or both, with the surgical instrument or components thereof to control its operation. The orientation sensor 30 may be powered by any suitable means, including, but not limited to, connection to the power source of the surgical instrument, battery, rechargeable battery, connection to a separate power source, and the like. The surgical instrument 1 may also comprise power supply. The power supply may comprise one or more batteries and/or other power storage device (e.g., capacitor) and/or a port for connecting to an external power supply. The one or more batteries may be rechargeable. The one or more batteries may comprise a lithium-ion battery (including thin film lithium ion batteries), a lithium-ion polymer battery, a nickel-cadmium battery, a nickel metal hydride battery, a lead-acid battery, combinations thereof, and the like. For example, an external power supply may supply power to the surgical instrument 1 and a battery may store at least a portion of the supplied power.

Accordingly, while a doctor generally has the use of their eyes when performing a medical procedure, it may be difficult to be able to see or otherwise discern the exact orientation of a particular surgical instrument, and use of the absolute orientation sensor 30 may be able to provide doctors with the exact orientation of a particular surgical instrument. It may be especially difficult to determine the orientation of this surgical instrument when part of the surgical instrument is inside a patient.

The absolute orientation sensor 30, utilizing its components, may determine various orientation factors of the surgical instrument 1, which may include location data, pitch data, roll data, and yaw data, angular velocity data, acceleration data, magnetic field strength data, linear acceleration data, gravity data, and temperature data. Location data may comprise x, y, and z coordinate values. Once orientation factors are determined or generated by the absolute orientation sensor 30, the absolute orientation sensor 30 may transmit a signal to the device processor 50. The device processor 50 may then transmit the signal in one or more ways to one or more different locations.

In one embodiment, the device processor 50 may transmit the signal comprising the orientation information to the display 70. The display 70 may digitally display the information received such that the user may read the information off of the display 70. In another embodiment, the device processor 50, may transmit the signal comprising the orientation information to the input/output device 85, which may then communicate via a communication link 87 with the remote device 80. The communication link 87 may be a wireless signal, wired signal, or other communication protocol. The remote device 80 may then display, or otherwise use, the orientation information. In another embodiment, the device processor 50 may transmit a signal, based on the received orientation information, to the audio device 95 to generate a sound. For example, where the orientation information received by the device processor 50 indicates that the surgical instrument 1 is not within specified parameters, the device processor 50 may send a signal to the audio device 95 to generate a sound, which signals to a user that the surgical instrument 1 should have its orientation corrected. The degree or intensity of the sound may correspond to how far outside the specified parameters the surgical instrument 1 is.

In an alternative embodiment, the device processor 50 may send a signal to the light source 60 controlling the light source 60 when one or more other conditions are met. For example, the device processor 50 may activate, or deactivate, the light source 60 when the surgical instrument 1 is in use, when one or more orientation conditions are met, when one or more orientation conditions are not met, or another trigger event. The light source 60 may include compact fluorescence lights, light emitting diodes, incandescent, fluorescent, halogen, and other types of lights.

In one embodiment of the surgical instrument 1, the information received by the remote device 80 may be used to create a real-time virtual image or representation of the surgical instrument 1 by the remote device 80.

Figure 2:
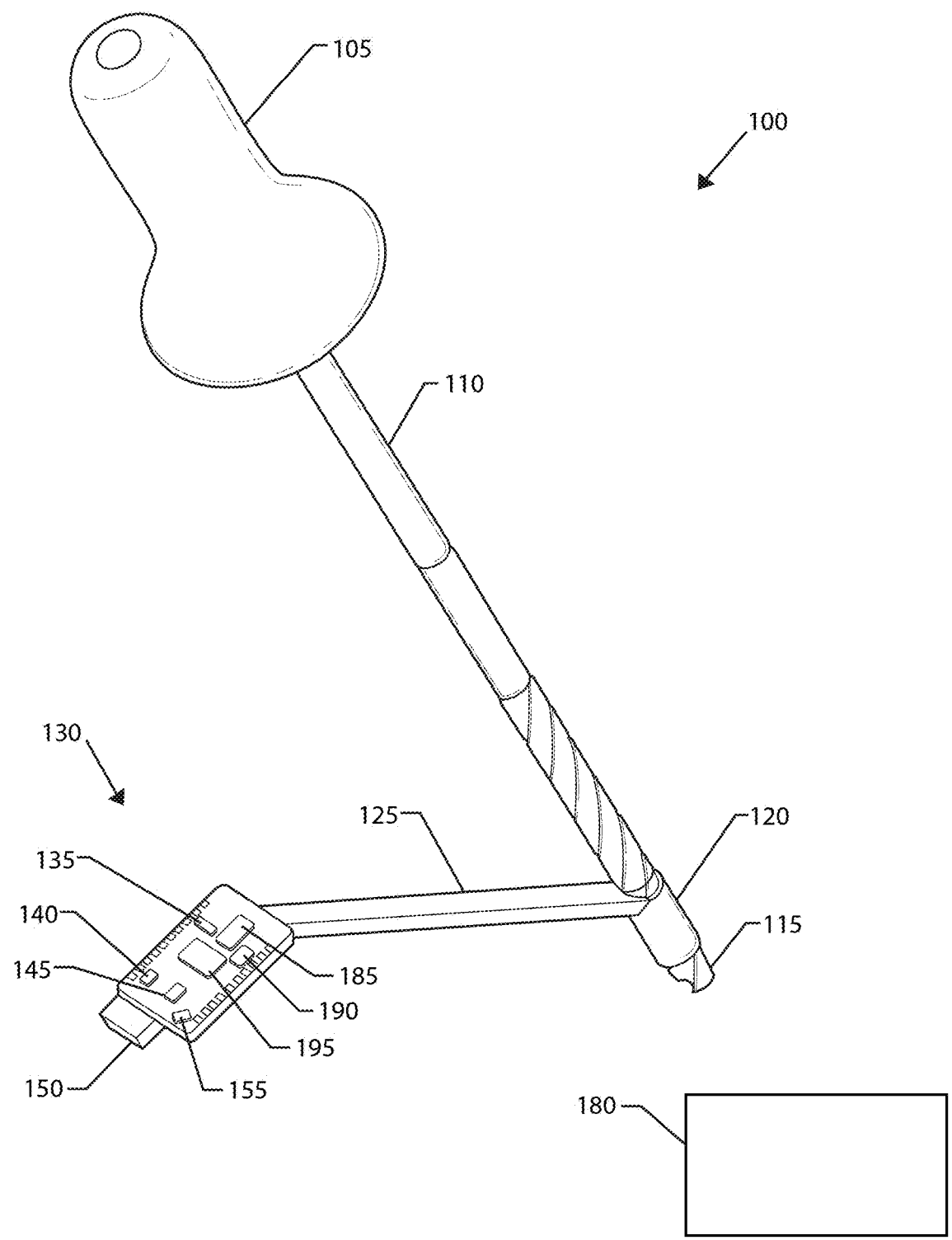
FIG. 2 is a perspective illustration of one embodiment of a surgical instrument that is a surgical awl according to the present disclosure.
Figure 3:
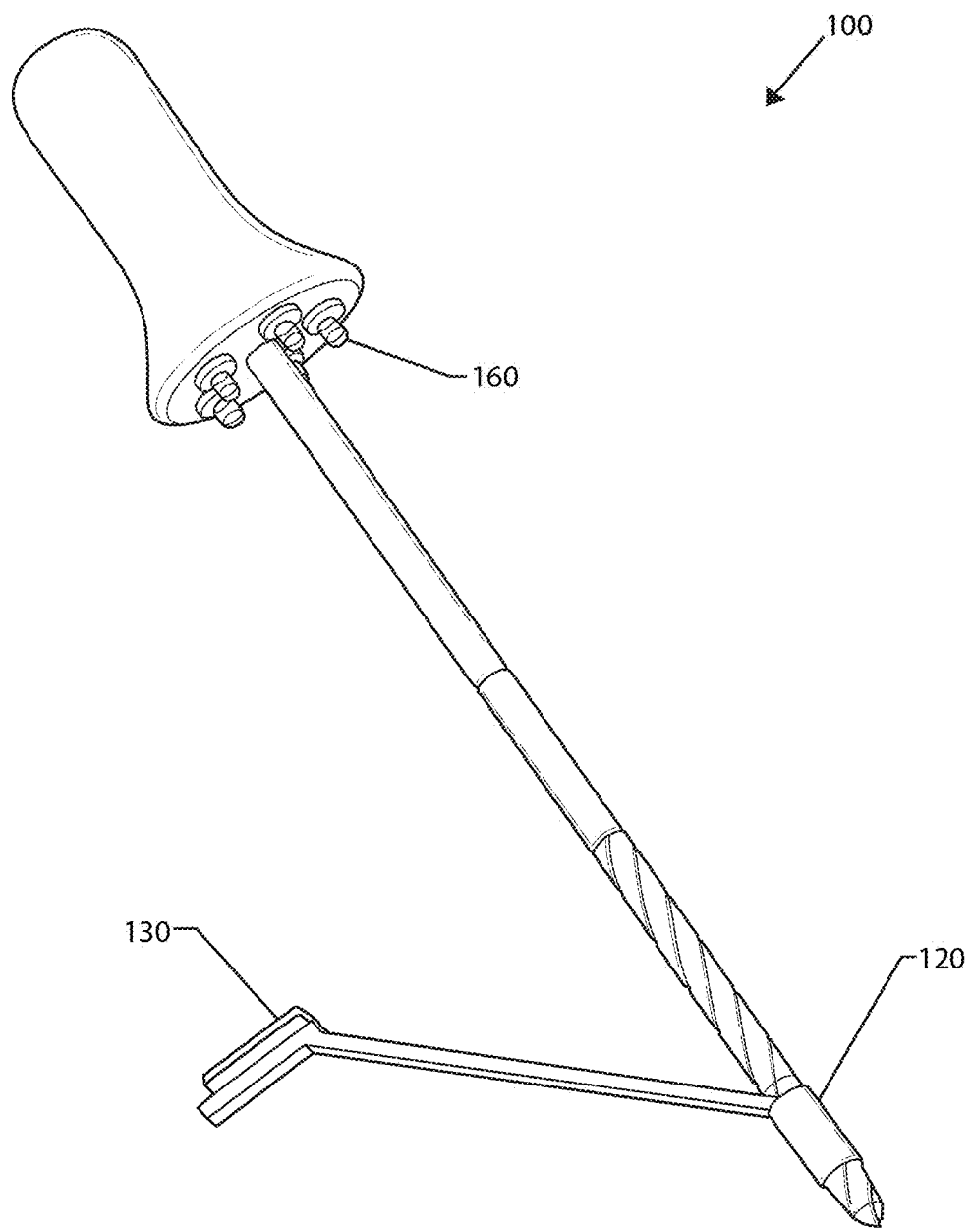
FIG. 3 is a side plan illustration of one embodiment of a surgical instrument that is a surgical awl according to the present disclosure.

FIG. 2 and FIG. 3 are illustrations of one embodiment of a surgical instrument that is a surgical awl according to the present disclosure. As shown in FIGS. 1 and 2, the surgical awl 100 may comprise a handle 105, neck 110, drill 115, rigid guide 120, sensor mounting portion 125, and absolute orientation sensor 130.

The handle 105 may be connected to a first end of the neck 110, and the drill 115 may be connected to a second and of the neck 110. The guide 120 may substantially encapsulate the drill 115, as shown, or alternatively the guide 120 may encapsulate the neck 110. In one embodiment, the sensor mounting portion 125 may be connected on a first end to the guide 120 and on a second end to the absolute orientation sensor 130. In the alternative embodiments, the absolute orientation sensor 130 may be mounted on substantially any portion of the surgical awl 100. The absolute orientation sensor 130 may be mounted to the surgical awl 100 by the use of an adhesive, screws, bolts, or any other connecting means. Alternatively, the absolute orientation sensor 130 may be built into the housing of the surgical awl 100.

The absolute orientation sensor 130 may comprise an accelerometer 135, gyroscope 140, magnetometer 145, device processor 150, and a power source 155.

The device processor 150 may control the absolute orientation sensor's 130 components.

The surgical awl 100 described herein may function substantially similarly to a standard medical awl, except that the surgical awl 100 provides additional orientation data to the doctor and illumination.

The orientation information generated by the absolute orientation sensor 130 may be relayed to a doctor by transmitting the orientation information to a digital display attached to a surgical instrument or to an external receiving electronic device. If the orientation information is being transmitted to an external receiving electronic device, the absolute orientation sensor 130 may comprise a wireless communication component to transmit the orientation information.

As shown in FIG. 3, the surgical awl 100 may also comprise a light source 160. The light source may be located on a proximal end of the handle 105, such that the light source 160 illuminates a portion of a patient to be operated upon. The light source 160 may interface wirelessly or wired, or both, with the surgical awl 100 or components thereof to control its operation. The light source 160 may be powered by any suitable means, including, but not limited to, connection to the power source of the surgical instrument, battery, rechargeable battery, connection to a separate power source, and the like. The light source 160 may also be a plurality of light sources, and may be located near to one another or spaced apart. In one embodiment, the light sources may be directed towards a common location such that the combination of light sources provides more lighting than a single light source would.

The surgical awl 100 may have a power source in the handle 105, or in another suitable location in order to power the light source 160 and the absolute orientation sensor 130.

The light source 160 (or another light source) may be configured to provide visual feedback to the user based on the orientation of the surgical awl 100. For example, the light source 160 may be configured to adjust the light output based on the orientation of the surgical awl 100 detected by the absolute orientation sensor 130 relative to a predetermined orientation.

In an embodiment, the one or more lights of the light source turn on/off or pulse based on whether the orientation of the awl is within a predetermined threshold of the predetermined orientation. For example, a lower light can be turned off when the handle of the awl is too low to inform the user that the handle needs to be raised.

In an embodiment, one or more lights of the light source may change color based on whether the orientation of the awl is within a predetermined threshold of the predetermined orientation. A red, yellow, or green color may indicate that the tool is out of position, close to position, or within a position (or within a predetermined threshold of the position) that is designated (e.g., by the user). For example, a green light may be generated when the orientation is within the predetermined threshold, and a red light may be generated when the orientation is outside of the predetermined threshold. The red light may be directed downward and/or a green light may be directed upward when the handle of the awl is too low to provide the user with feedback regarding how the orientation of the awl should be to better match the predetermined orientation.

In some embodiments, the light source is configured to adjust based on a predetermined fixed angle or position value. For example, one or more lights of the lights source may light up in a predetermined orientation, sequence, and/or pattern to indicate that the tool is being used at a predetermined orientation or predetermined orientation relative to a designated orientation.

In some embodiments, a display or other visual feedback is provided to inform the user of the orientation of the awl relative to the predetermined orientation. For example, the lighting and/or other display feedback can indicate to the user differential orientation about translation and/or rotation in three-dimensional space. Such feedback may be in real-time.

The light source 160 may be configured to communicate (e.g., wirelessly) with the device processor 150 to provide feedback in real-time based on the current position of the absolute orientation sensor 130 and the surgical awl 100.

For example, the user can input a desired orientation in the x, y, z planes, and the instrument lighting can turn on/off and change color intermittently based on the current orientation to provide feedback to the user about the orientation. Independent differential feedback in each plane that can account for degrees of mis-alignment from a desired orientation can allow the user to know how to adjust the instrument to achieve the desired orientation.

In some embodiments, the absolute orientation sensor and/or the surgical awl is configured to provide audio and/or tactile feedback to the user based on whether the orientation of the awl is within a predetermined threshold of the predetermined orientation.

In an embodiment, the light source is configured to indicate that one portion of the instrument is parallel, perpendicular to, or any orientation with respect to another portion of the instrument. The indication from the light source allows the user to know whether the sleeve and the drill are coaxial with one another. The light source may be configured to communicate with the both instruments and provide visual feedback based on whether the instruments are within a predetermined coaxial threshold. The sleeve and the drill may have independent absolute orientation sensors and may communicate orientation information to one another.

The surgical awl 100 may also comprise a remote device 180, input/output device 185, communication link 190, and audio device 195. As described hereinbelow, the input/output device 185 may transmit information generated by the absolute orientation sensor 130 and processed by the device processor 150 to the remote device 180. The input/output device 185 may utilize the communication link 190 to transmit information wirelessly to the remote device 180. Additionally, the input/output device may transmit a signal to the audio device 195 to cause the audio device to provide an audio notification based on the orientation information generated by the absolute orientation sensor.

In alternative embodiments, the surgical instrument may be any instrument suitable for surgical or medical procedures or treatments on humans or animals. The surgical instrument may be made of titanium, aluminum, stainless steel, various alloys, as well as various plastics. The surgical instrument may include a housing or other outer structure to which the lighting source may be attached or affixed. In an example embodiment, the light source 160, may include a trigger mechanism or component which operates in conjunction with the operation of the surgical instrument. This may allow the light source 160 to emit light upon operation of the surgical instrument, synchronizing the operation of the light source 160 with the function of the surgical instrument. The light source 160 may include compact fluorescence lights, light emitting diodes, incandescent, fluorescent, halogen, and other types of lights.

Figure 4:
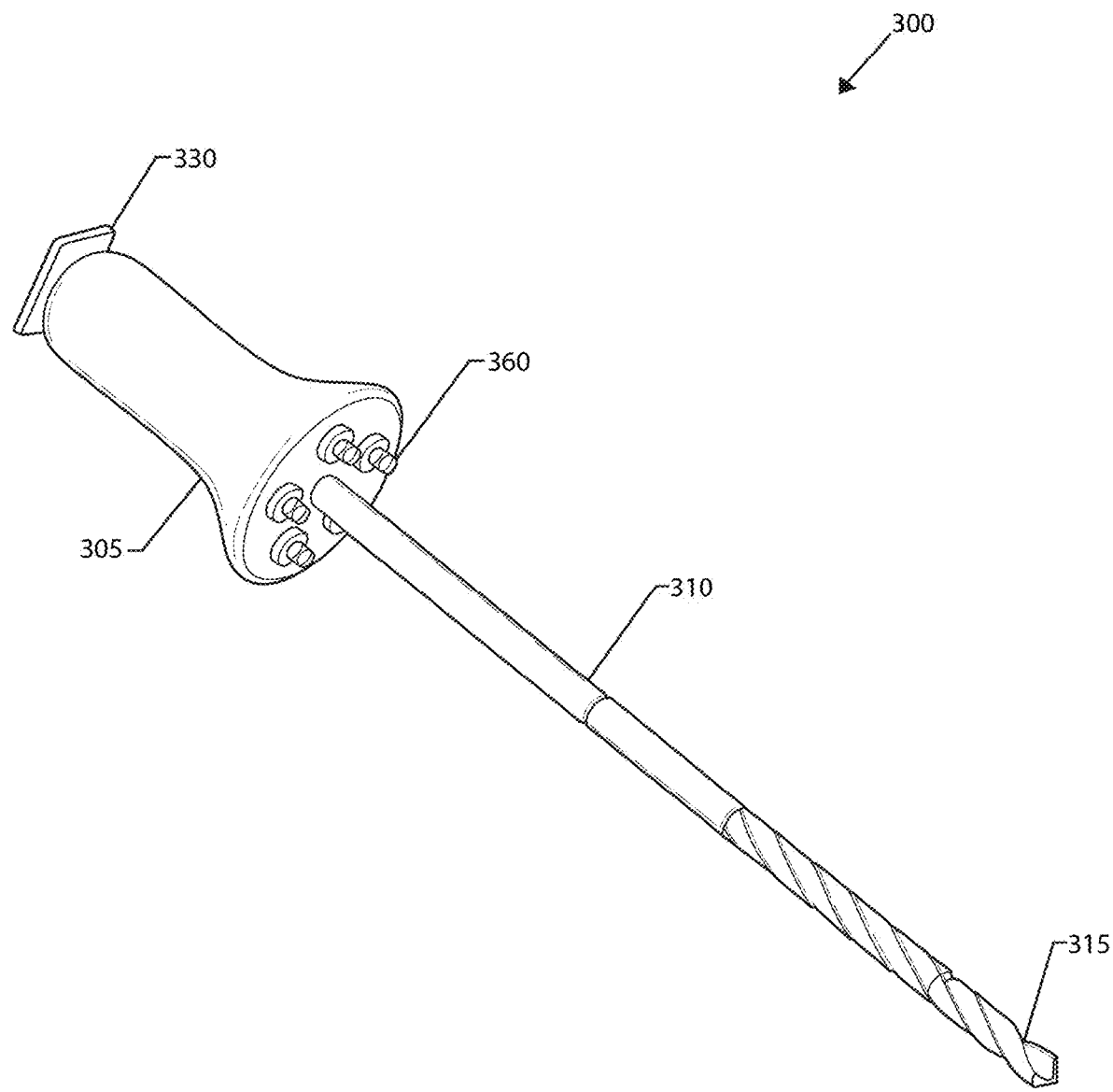
FIG. 4 is a front perspective illustration of an alternative embodiment of a surgical instrument that is a surgical awl according to the present disclosure.
Figure 5:
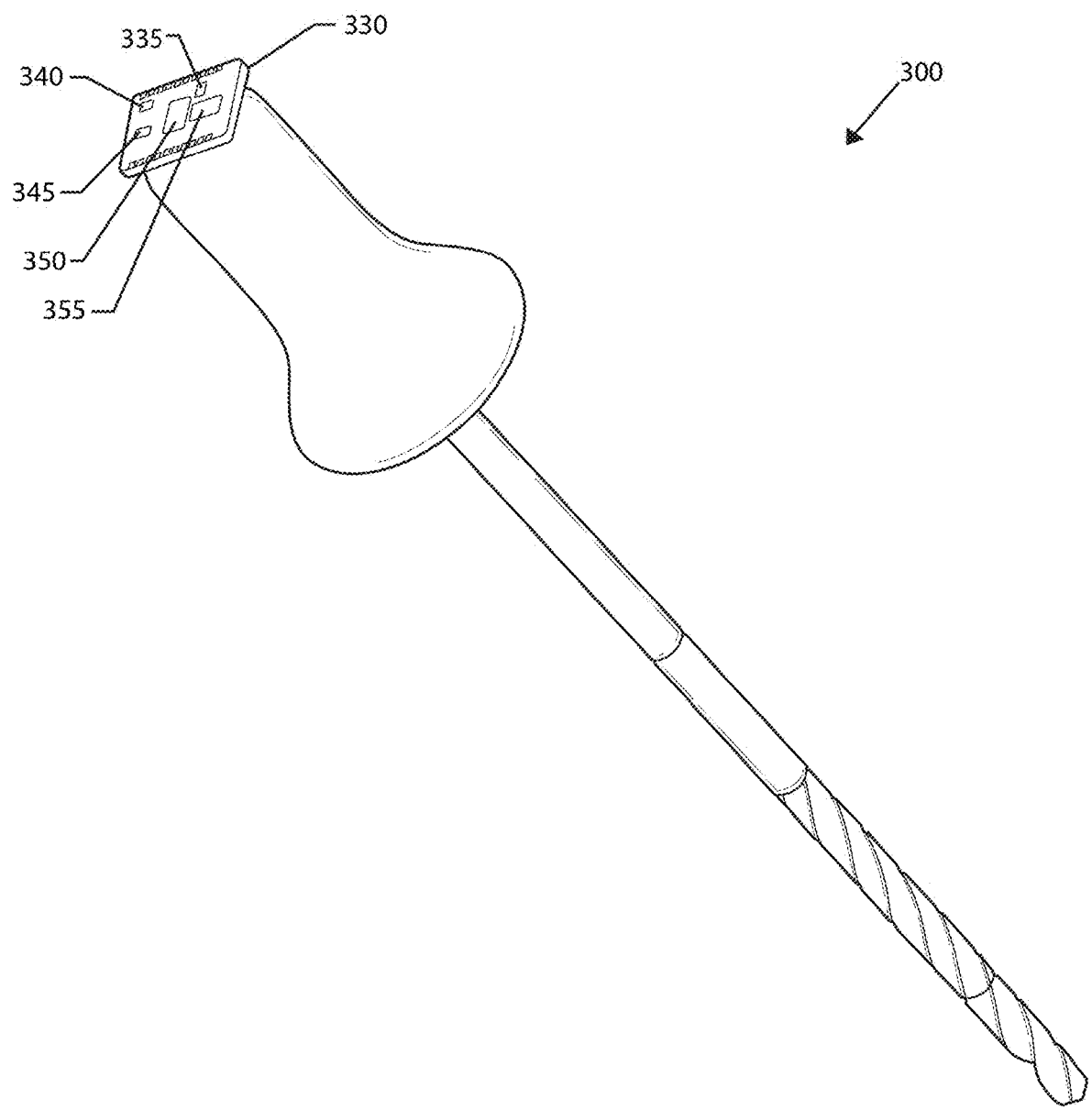
FIG. 5 is a rear perspective illustration of an alternative embodiment of a surgical instrument that is a surgical awl according to the present disclosure.

FIG. 4 and FIG. 5 are illustrations of an alternative embodiment of a surgical instrument that is a surgical awl according to the present disclosure. As shown in FIGS. 4 and 5, an alternative embodiment of a surgical awl 300 may comprise a handle 305, neck 310, drill 315, light source 360, and absolute orientation sensor 330.

The handle 305 may be connected to a first end of the neck 310, and the drill 315 may be connected to a second and of the neck 310. The absolute orientation sensor 330 may be located on a distal end of the handle 305.

As shown in FIG. 4, the surgical awl 300 made comprise a light source 360. The light source 360 may be located on a proximal end of the handle 305, such that the light source 360 illuminates a portion of a patient to be operated upon.

The surgical awl 300 may have a power source in the handle 305, or in another suitable location in order to power the light source 360 and the absolute orientation sensor 330.

Figure 6:
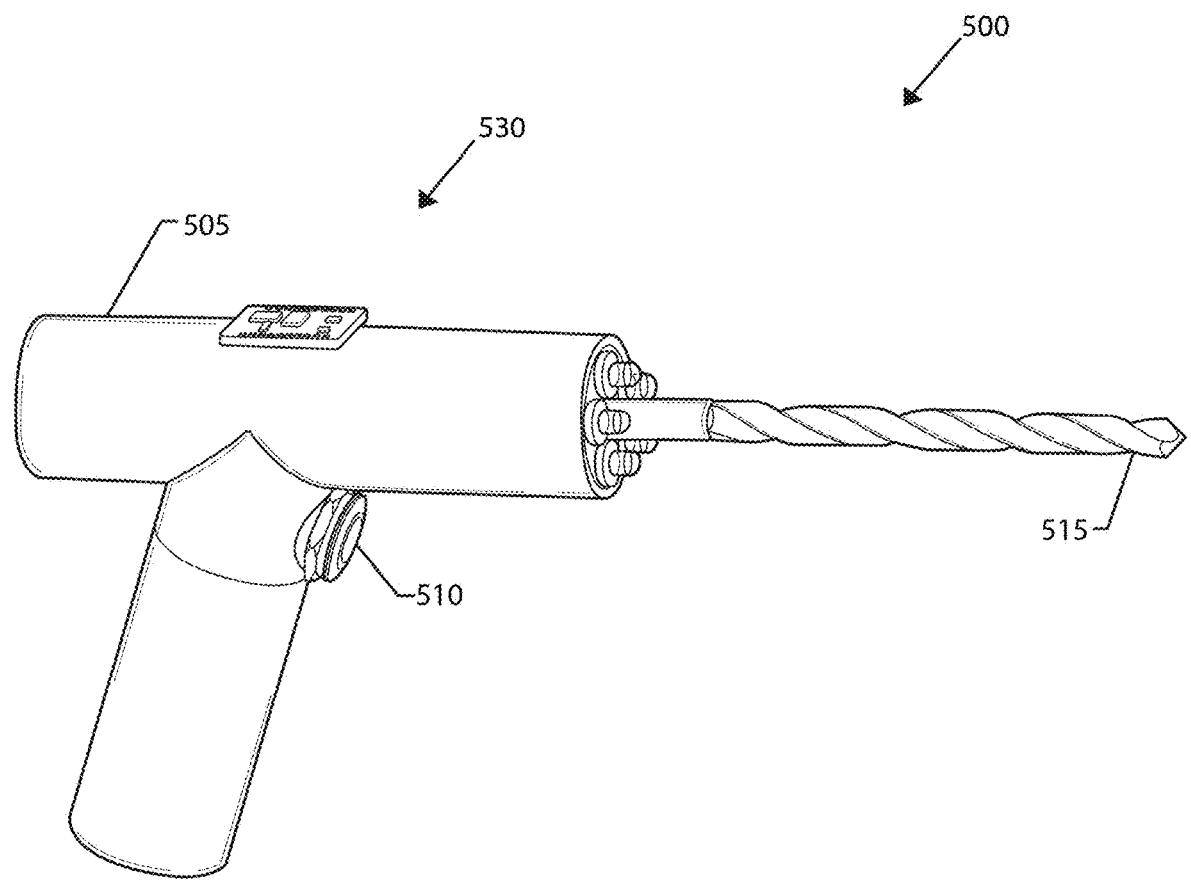
FIG. 6 is a side perspective illustration of an embodiment of a surgical instrument that is a surgical drill according to the present disclosure.
Figure 7:
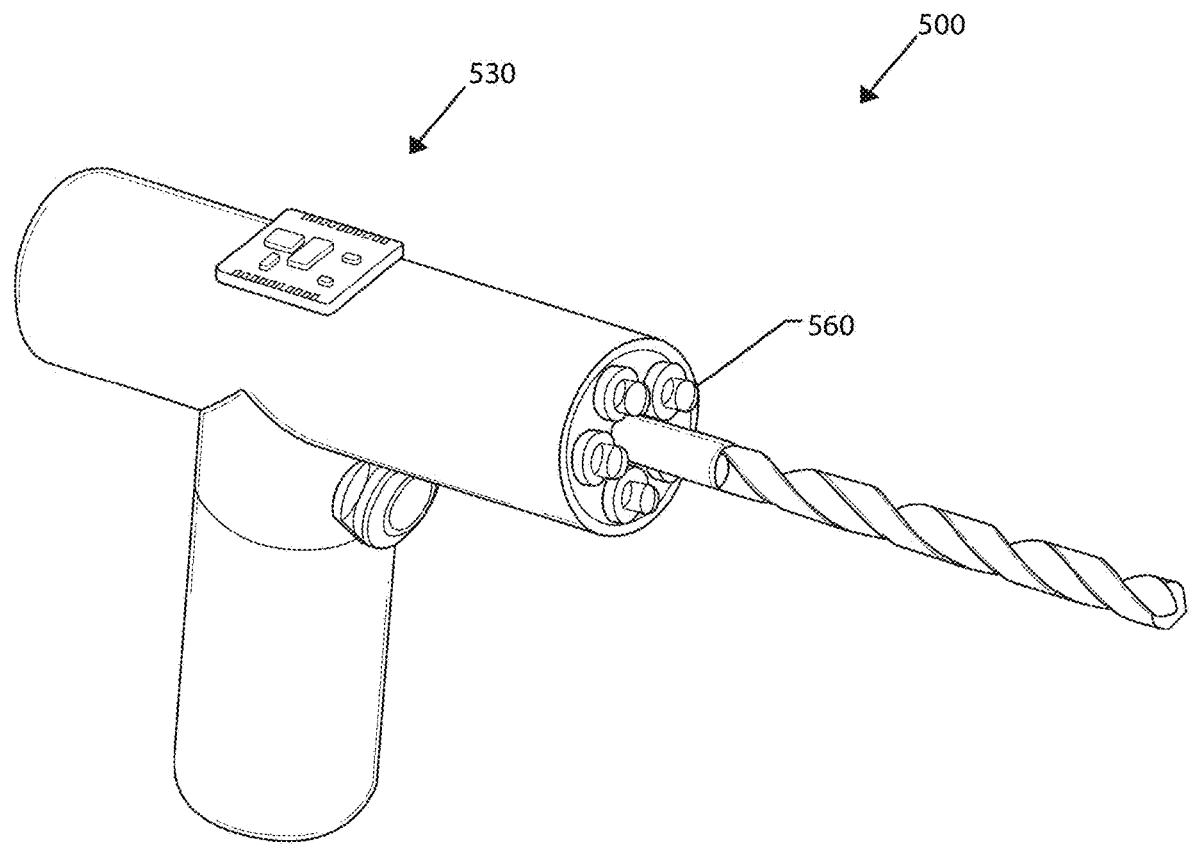
FIG. 7 is a front perspective illustration of an embodiment of a surgical instrument that is a surgical drill according to the present disclosure.

FIG. 6 and FIG. 7 are illustrations of an embodiment of a surgical instrument that is a surgical drill according to the present disclosure. The surgical drill 500 may comprise, a housing 505, trigger 510, drill 515, absolute orientation sensor 530, and light source 560. The trigger 510 may be mounted on a handle portion of the housing 505, and the drill 515 may extend from a forward portion of the housing 505. The light source 560 may be mounted near where the drill 515 and housing 505 connect. As shown in FIGS. 6 and 7, the absolute orientation sensor 530 may be located on top of the housing 505. In an alternative embodiment, the absolute orientation sensor 530 may be located on a different part of the housing 505. The absolute orientation sensor 530 may function substantially similarly to the one described in FIGS. 2-3.

A power source may be contained within the housing 505, such that the power source is able to power the drill 515, the light source 560, and/or the absolute orientation sensor 530. In one embodiment, when the trigger 510 is depressed the drill 515 and the light source 560 are activated substantially simultaneously. In a preferred embodiment, the absolute orientation sensor 530 is active independent of the trigger 510.

Figure 8:
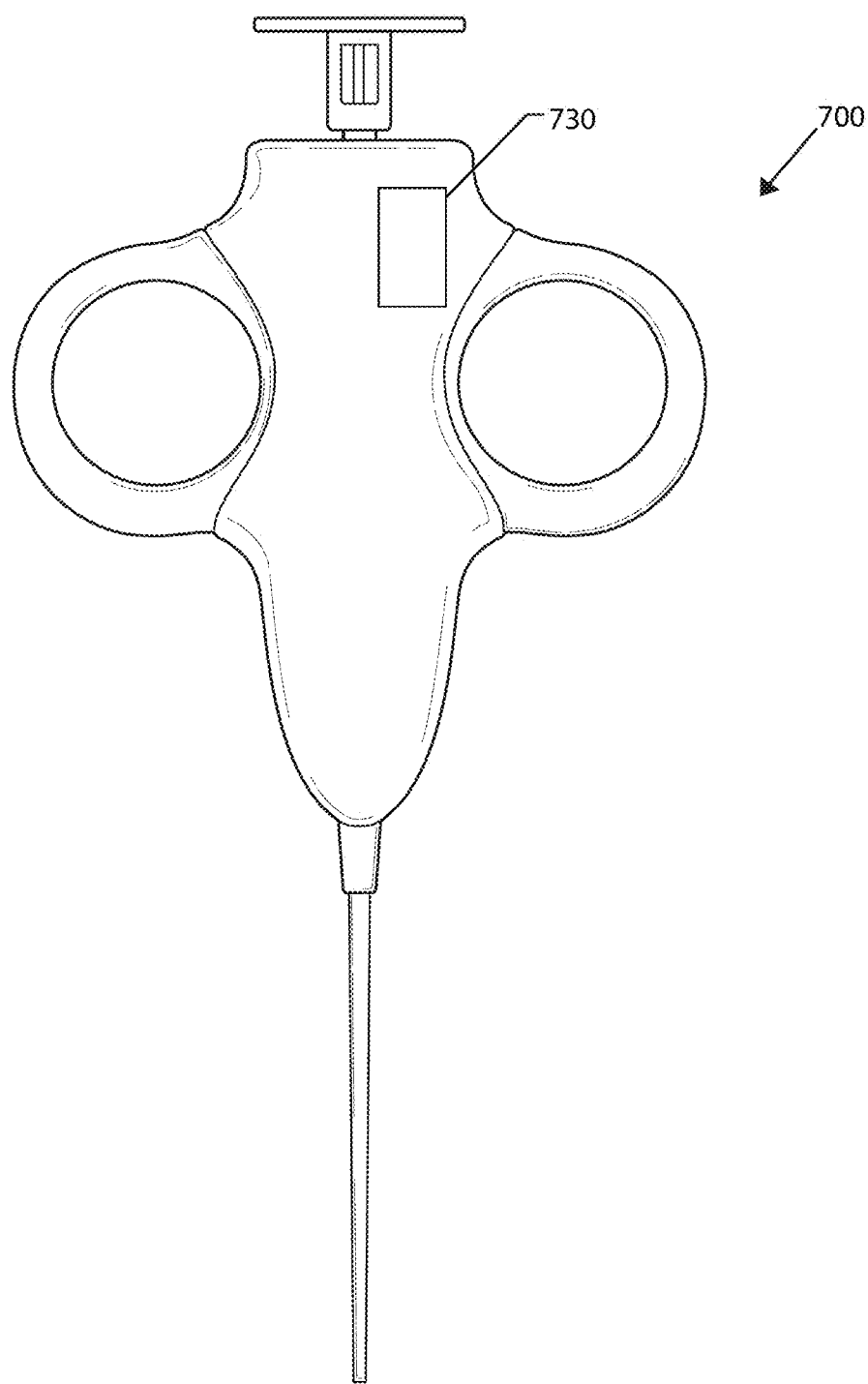
FIG. 8 is an illustration of one embodiment of a surgical instrument that is a biopsy needle according to the present disclosure.

FIG. 8 is an illustration of one embodiment of a surgical instrument that is a biopsy needle according to the present disclosure. As shown in FIG. 8, the biopsy needle may comprise an absolute orientation sensor 730. The biopsy needle 700 generally comprises a hollow needle that may be inserted into an area from which a sample is desired. The biopsy needle 700 is useful in obtaining samples of certain tissues, including liver, kidney, and the genitourinary tract, skin, breast, lung, bone, prostate, testicle, intestine, brain, ovary, uterus, and thyroid, in addition to other tissue types, as well as fluid collections, abscesses, tumor, hematoma, and other masses, fluids, collections, and area of interest for potential biopsy. The biopsy needle 700 may have additional gripping portions to allow a user to more accurately and steadily use the needle to recover a sample of soft tissue. In some embodiments, the biopsy needle may be hollow, and after inserted such that a desired sample is now present in the hollow needle, a blight suction may be applied to keep the core sample inside the needle wild and needle is removed from soft tissue.

Figure 9:
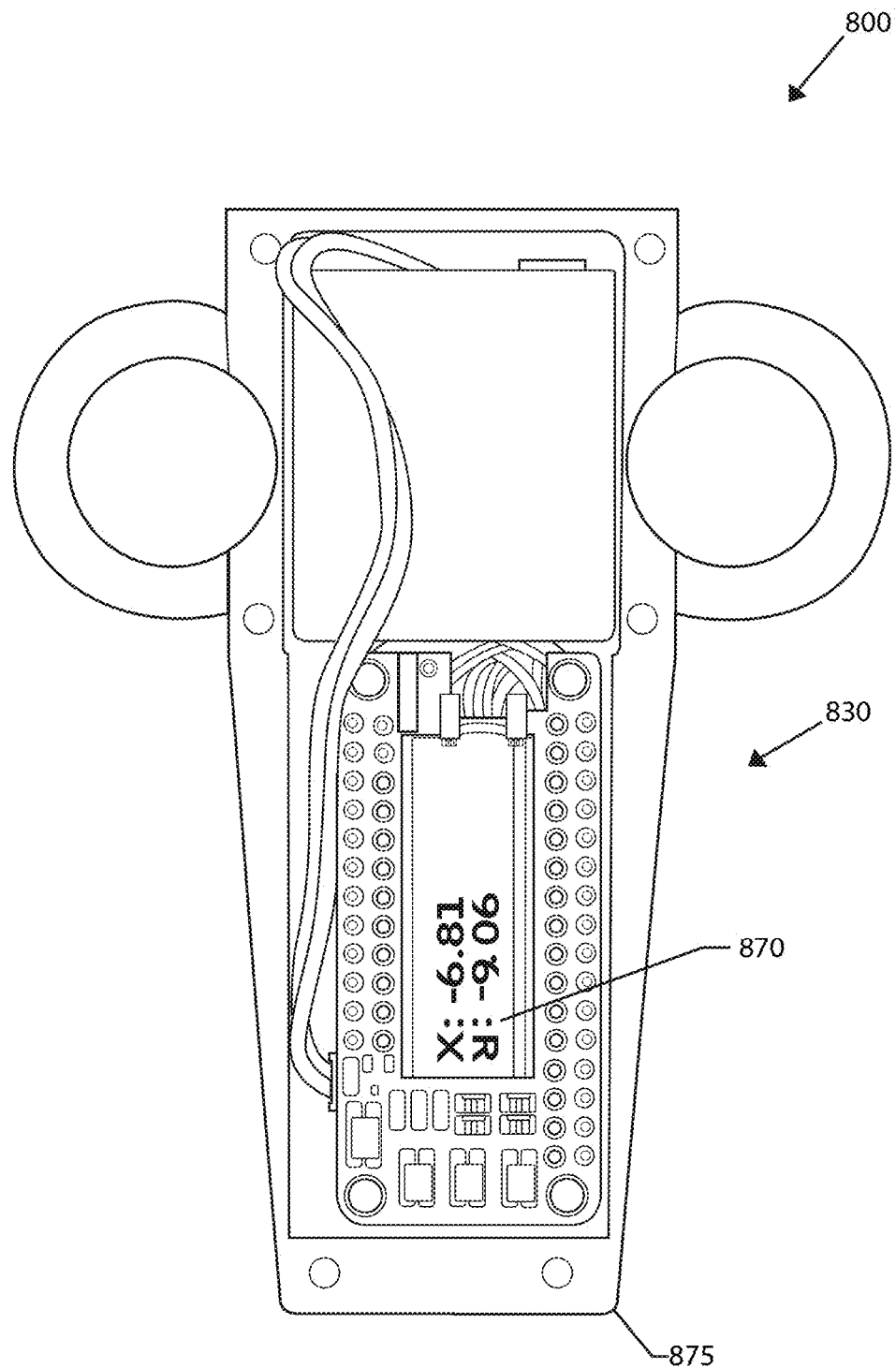
FIG. 9 is an illustration of one embodiment of an absolute orientation sensor and display.

FIG. 9 is an illustration of one embodiment of an absolute orientation sensor and display. As shown in FIG. 9, the absolute orientation sensor and display 800 may comprise an absolute orientation sensor 830, display 870, and electronic housing 875. The electronic housing 875 may encapsulate the absolute orientation sensor 830 and the display 870. The electronic housing 875 may be configured to protect the absolute orientation sensor 830 and the display 875. In one embodiment, the electronic housing 875 may include a transparent portion to allow a user to view the display 870. Alternatively, the display 870 may be mounted on the outside of the electronic housing 875. The electronic housing 875 may be different shapes to accommodate different surgical tools. For example, as shown in FIG. 9, the electronic housing 875 may form of a shape that is consistent with this shape of a biopsy needle. It is understood that the electronic housing 875 that may take various shapes and make up portions of surgical instruments.

Figure 10:
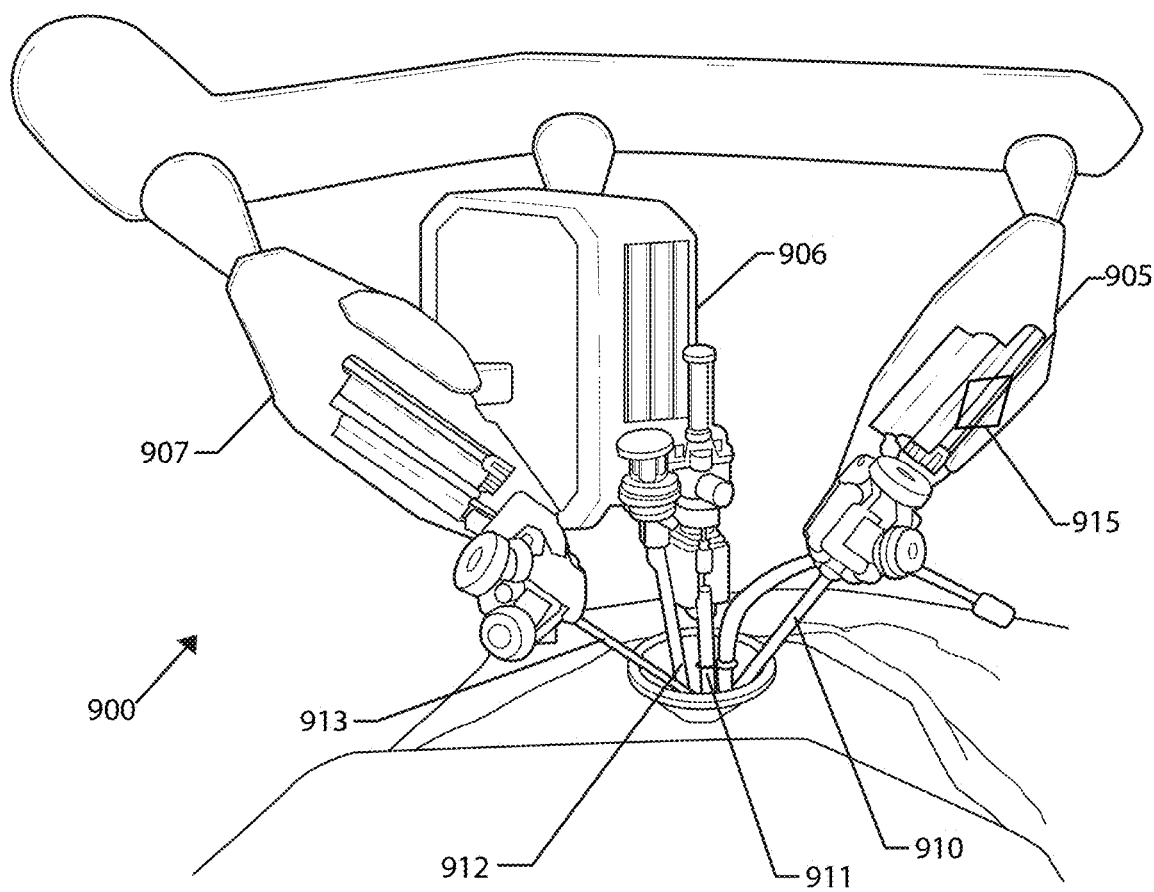
FIG. 10 is an illustration of one embodiment of a surgical instrument that is a robotic arm according to the present disclosure.

FIG. 10 is an illustration of one embodiment of a surgical instrument that is a robotic arm according to the present disclosure. As shown in FIG. 10, the robotic arm 900 may comprise mounting arms 905, 906, 907 robotic tools 910, 911, 912, 913 and an absolute orientation sensor 915. The robotic arm 900 may comprise any number of mounting arms 905, 906, 907 suitable for the surgery to be performed. Each of the mounting arms 905, 906, 907 may comprise any number of robotic tools 910, 911, 912, 913 suitable for the surgery to be performed. The robotic tools 910, 911, 912, 913 may be substantially any surgical device.

The absolute orientation sensor 915 may be substantially similar to the absolute orientation sensor 800 described in FIG. 9, and may or may not include a digital display. The absolute orientation sensor 915 may be mounted on the mounting arm 905. Alternatively, the absolute orientation sensor may be located on or in any of the mounting arms 905, 906, 907 and/or robotic tools 910, 911, 912, 913. Additionally, there may be multiple absolute orientation sensors 915 on different components of the robotic arm 900 at the same time.

In an embodiment, the surgical instrument may also comprise an input/output device coupled to a device processor, absolute orientation sensor, and/or any other electronic component of the surgical instrument. Input may be received from the device processor or absolute orientation sensor and/or output may be provided to an electronic display or another device via the input/output device. The input/output device may comprise any combinations of input and/or output devices such as buttons, knobs, keyboards, touchscreens, displays, light-emitting elements, a speaker, and/or the like. In an embodiment, the input/output device may comprise an interface port such as a wired interface, for example a serial port, a Universal Serial Bus (USB) port, an Ethernet port, or other suitable wired connection. The input/output device may comprise a wireless interface (not shown), for example a transceiver using any suitable wireless protocol, for example Wi-Fi (IEEE 802.11), Bluetooth®, infrared, or other wireless standard. For example, the input/output device may communicate with a remote device via Bluetooth® such that the data generated by the absolute orientation sensor may be sent to the remote device and monitored. In an embodiment, the input/output device may comprise a user interface.

The user interface may comprise at least one of lighted signal lights, gauges, boxes, forms, check marks, avatars, visual images, graphic designs, lists, active calibrations or calculations, 2D interactive fractal designs, 3D fractal designs, 2D and/or 3D representations of vapor devices and other interface system functions.

In an embodiment, the input/output device may comprise a touchscreen interface and/or a biometric interface. For example, the input/output device may include controls that allow the user to interact with and input information and commands to the surgical instrument. For example, with respect to the embodiments described herein, the input/output device may comprise a touch screen display. User inputs to the touch screen display are processed by, for example, the input/output device and/or the device processor. The input/output device may also be configured to process new content and communications to the surgical instrument. The touch screen display may provide controls and menu selections, and process commands and requests. Application and content objects may be provided by the touch screen display. The input/output device and/or the device processor may receive and interpret commands and other inputs, interface with the other components of the surgical instrument as required. In an embodiment, the touch screen display may enable a user to view at least one orientation data of the surgical instrument generated by the absolute orientation sensor.

In an embodiment, the input/output device may comprise an audio user interface. A speaker may be configured to send audio signals and relay the audio signals to the input/output device. The audio user interface may be any interface that is responsive to data generated. The audio user interface may be configured to transmit a sound based on the data generated by the absolute orientation sensor. The audio user interface may be deployed directly on the surgical instrument and/or via other electronic devices (e.g., electronic communication devices, such as a smartphone, a smart watch, a tablet, a laptop, a dedicated audio user interface device, other personal computing devices, and the like). The audio user interface may be used to convey data generated by the absolute orientations sensor. Such conveyance may comprise, but is not limited to, orientation data of the surgical instrument. The user may then adjust the positioning of the surgical instrument based on the audio signal output The input/output device may be configured to interface with other remote devices, for example, computing equipment, communications devices and/or other surgical devices, for example, via a physical or wireless connection. The input/output device may thus exchange data with the other equipment. A user may sync their surgical equipment to other devices, via programming attributes such as mutual dynamic link library (DLL) 'hooks'. This enables a smooth exchange of data between devices, as may a web interface between devices. The input/output device may be used to upload one or more orientation data to the other devices. Using monitoring equipment as an example, the one or more orientation data may comprise data such as location data, pitch data, roll data, yaw data, x, y, and z coordinate values, angular velocity data, acceleration data, magnetic field strength data, linear acceleration data, gravity data, and temperature data. Data from usage of previous monitoring sessions may be archived and shared.

In general, the embodiments herein provide surgical and medical instruments having high intensity lighting and/or absolute orientation sensors. The instruments of the present disclosure may be used in any suitable procedure or treatment which would benefit from high intensity lighting of the area to be treated or of interest, as well as knowing the orientation of such instrument in three-dimensional space. While reference is made herein to surgical instruments in particular, it should be understood that this disclosure is directed to medical, dental, or other instruments used in the treatment of humans or animals requiring lighting and/or absolute orientation.

As discussed above, the surgical instrument is any instrument suitable for surgical or medical procedures or treatments on humans or animals. The surgical instrument may be comprised of titanium, aluminum, stainless steel, various alloys, as well as various plastics. The surgical instrument may include a housing or other outer structure to which the absolute orientation sensor may be attached or affixed. In an example embodiment, the orientation sensor can include a trigger mechanism or component which operates in conjunction with the operation of the instrument.

As discussed above, any suitable surgical instrument can include the high intensity lighting source or the absolute orientation sensor, or both. Examples include, but are not limited to, powered instruments, such as drills/drivers, saws, wire insertion devices, burr, and the like, and manual instruments, such as awls for pedicle screw placement, scalpels, suction, retraction devices, mallets, unpowered drills, drivers, saws, wire inserters, and burrs, and various hand tools. Surgical instruments including such high intensity lighting source and/or absolute orientation sensor can be used in any suitable procedure, treatment, or field. Examples, include, but are not limited to: orthopedic surgery, including but not limited to: spine surgery, orthopedic trauma surgery, foot and ankle surgery, sports surgery, joint replacement in knee, hip, shoulder, any fracture fixation, tibial, femoral, and other long bone nailing procedures, upper extremity and hand surgery, oncological orthopedic surgery, and pediatric orthopedic surgery; neurological surgery, including but not limited to: spine surgery, intracranial surgery of all kinds, and surgery in central and peripheral nervous systems; otolaryngology surgery; plastic surgery, obstetric and gynecological surgery, urological surgery, trauma surgery, general surgery; anesthesia; emergency medicine; family and internal medicine; gastroenterology; cardiology; dental surgery; veterinary surgery; and all surgical and medical fields not named above.

Having thus described certain embodiments for practicing aspects of the present disclosure, it is to be appreciated that various alterations, modifications, and improvements will readily occur to those skilled in the art. Such alterations, modifications, and improvements are intended to be part of this disclosure, and are intended to be within the spirit and scope of this disclosure.

Figure 11:
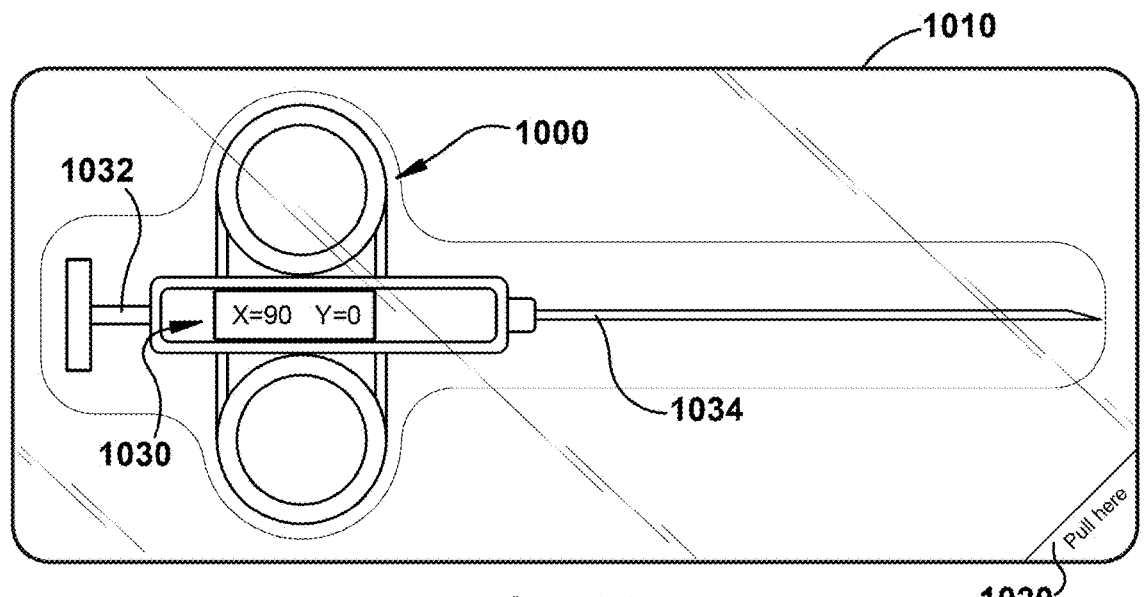
FIG. 11 is a front illustration of another embodiment of a surgical instrument enclosed within hermetically sealed packaging.

Turning now to FIG. 11, an exemplary embodiment of a biopsy needle is shown at 1000. The biopsy needle 1000 is substantially the same as the above-referenced biopsy needle 700, and consequently the same reference numerals but indexed by 1000 are used to denote structures corresponding to similar structures in the biopsy needle 1000. In addition, the foregoing description of the biopsy needle 700 is equally applicable to the biopsy needle 1000 except as noted below. Moreover, it will be appreciated that aspects of the biopsy needles may be substituted for one another or used in conjunction with one another where applicable.

The biopsy needle 1000 may be sterile and enclosed in packaging 1010 that hermetically seals the biopsy needle 1000 from the environment. For example, the packaging 1010 may include a pull tab 1020 that allows a user to remove the biopsy needle 1000 from the packaging 1010 by hand when the user desires to use the biopsy needle 1000.

The packaging 1010 may be made of plastic or another suitable material that protects the biopsy needle 1000 from the environment and allows the biopsy needle 1000 to be removed from the packaging 1010 by a user. In an embodiment, the packaging is be made of plastic, resin, metal, paper, or glass and/or is not configured to withstand several rounds of sterilization. As discussed further below, the packaging 1010 may be disposed of after the biopsy needle 1000 is removed from the packaging 1010.

The biopsy needle 1000 may include an absolute orientation sensor 1030, which may be permanently fixed to a main body 1032 and a needle portion 1034 of the biopsy needle 1000. In another embodiment, the absolute orientation sensor may be detached from the remainder of the biopsy needle.

After the user is done using the biopsy needle 1000 the entire biopsy needle 1000 may be disposed of. As described above, the absolute orientation sensor 1030 may include, but is not limited to a 9-degree of freedom sensor system, and/or inertial measurement unit (IMU) that may integrate sensory input from an accelerometer, gyroscope, and magnetometer to provide orientation data from the medical device or instrument to the user.

In an embodiment, the absolute orientation sensor can be a disposable attachment to a medical device that is reusable—or components of a medical device that are reusable (e.g., the main body of a biopsy needle). In another embodiment, absolute orientation sensor can take the form of a reusable package integrated into a disposable device. Other embodiments include any combination of the reusable and disposable features discussed above.

Disposability adds a novel use to the above described or other medical devices. Due to advances made in technology particularly in the field of cellular telephone and communication equipment, the absolute orientation sensor 1030 can be integrated into a medical device in such a fashion that the device can be discarded at the end of the medical procedure. This may not necessitate a significant change in physician behavior or require additional time for hospital staff. For example, an interventional radiologist at the end of a procedure may dispose of the biopsy needle 1000, instead of recycling or reusing the biopsy needle 1000. Thus, disposing of the biopsy needle 1000 allows the radiologist to use the biopsy needle 1000 and dispose of it without requiring significantly more time or a significant behavior change.

Furthermore, disposability can avoid the need for sterilization just prior to use by medical staff. For example, the biopsy needle 1000 can be discarded after a single use thereby avoiding any need for hospital staff to use a sterilization process on the entire biopsy needle 1000 (e.g., via a chemical, gas, steam, UV or the like sterilization process). The biopsy needle 1000 thus allows hospital staff to avoid costly, time-intensive, and environmentally-unfriendly sterilization practices.

Figure 12:
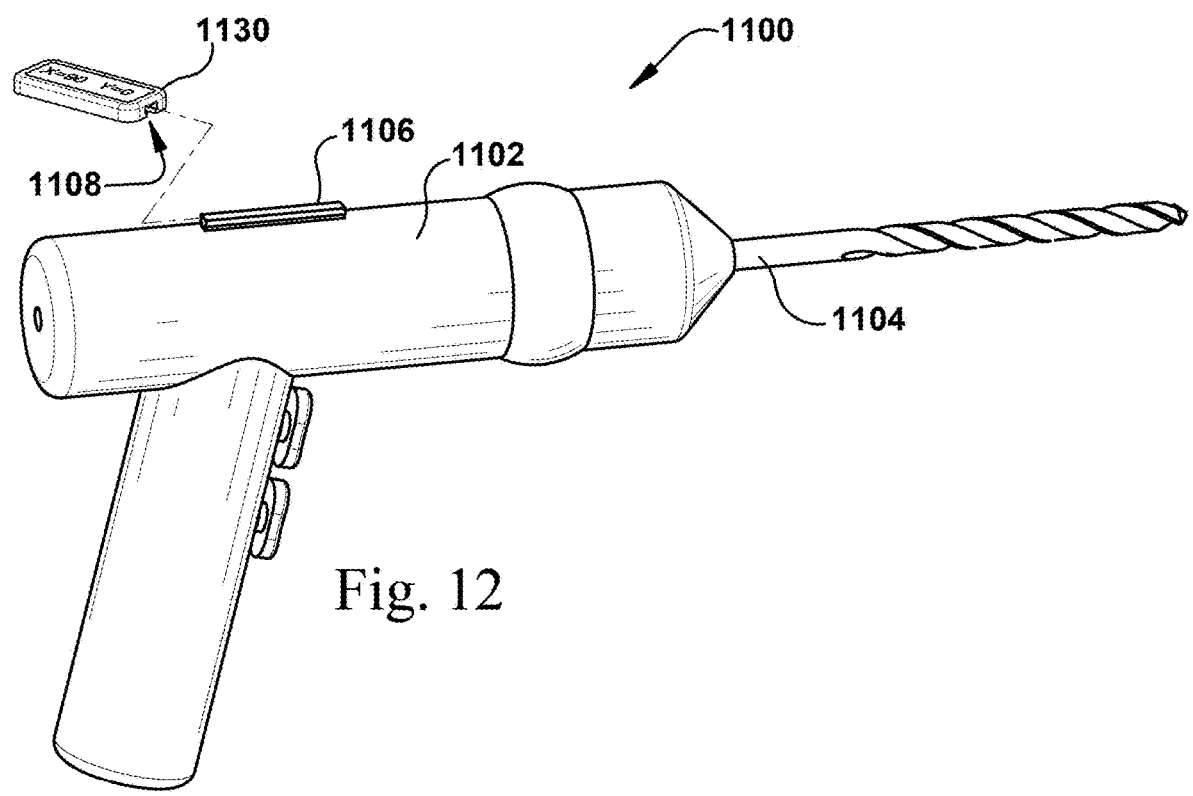
FIG. 12 is a front perspective illustration of another embodiment of a surgical instrument with a detachable absolute orientation sensor that is able to attach to an instrument body of the surgical instrument.
Figure 13:
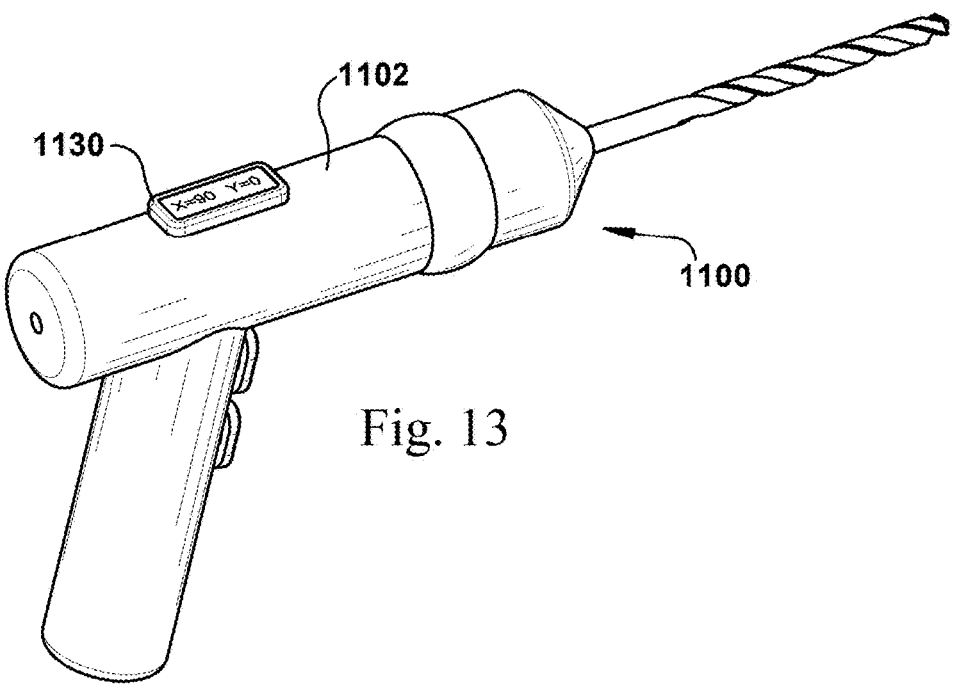
FIG. 13 is a front perspective illustration of the surgical instrument of FIG. 12 with the absolute orientation sensor attached.
Figure 14:
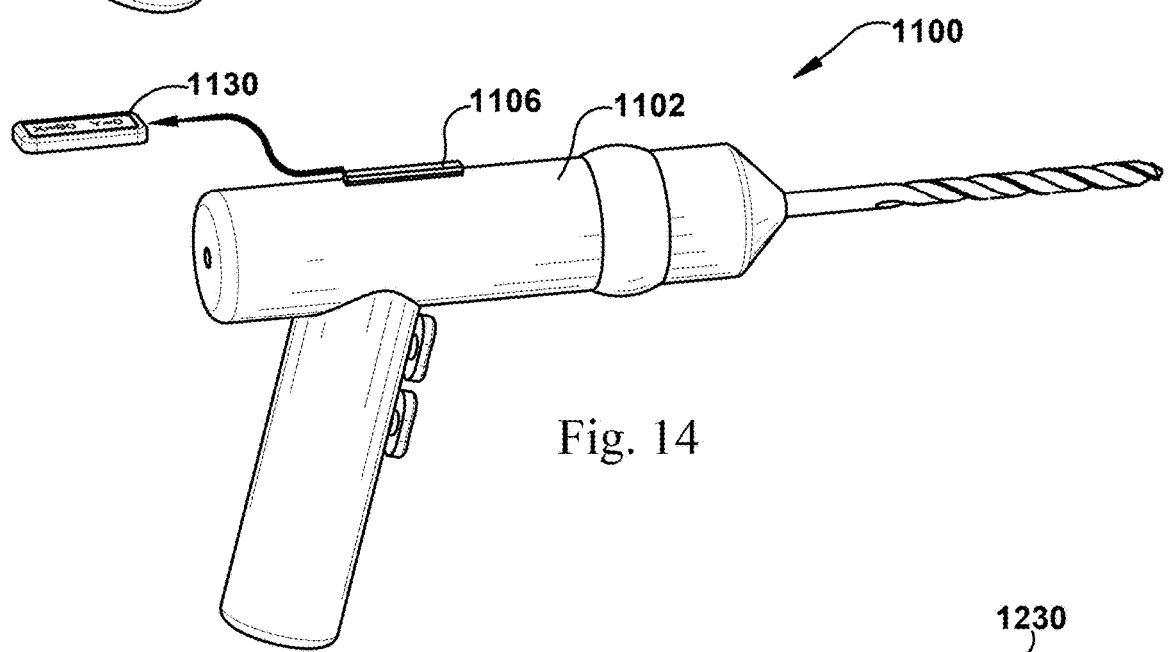
FIG. 14 is a front perspective illustration of the surgical instrument of FIG. 12 with the absolute orientation sensor detached.

Turning now to FIGS. 12-14, an exemplary embodiment of a surgical drill is shown at 1100. The surgical drill 1100 is substantially the same as the above-referenced surgical drill 500, and consequently the same reference numerals but indexed by 1100 are used to denote structures corresponding to similar structures in the surgical drill 1100. In addition, the foregoing description of the surgical drill 500 is equally applicable to the surgical drill 1100 except as noted below. Moreover, it will be appreciated that aspects of the surgical drills may be substituted for one another or used in conjunction with one another where applicable.

Referring initially to FIG. 12, the surgical drill 1100 may include a housing 1102 (an example of an instrument body), a drill bit 1104 (an example of an instrument body), and a detachable absolute orientation sensor 1130. The housing 1102 may be configured to attach to and detach from the absolute orientation sensor 1130. For example, the housing 1102 and the absolute orientation sensor 1130 may attach to one another via a T-shaped (or a dovetail) connection.

The housing 1102 may include a T-shaped (or dovetail shaped) protrusion 1106 that is configured to slide into a similarly shaped groove 1108 of the absolute orientation sensor 1130 to form a press-fit attachment. When attached, the absolute orientation sensor 1130 may move entirely with the housing 1102.

FIGS. 12-14 illustrate attachment and detachment of the absolute orientation sensor 1130 from the housing 1102. Referring again to FIG. 12, the absolute orientation sensor 1130 may be attached to the protrusion 1106 by aligning the front of the groove 1108 with the back of the protrusion 1106 and sliding the groove 1108 toward the front of the housing 1102 until the protrusion 1106 is press-fit to the groove 1108. In another embodiment, the absolute orientation sensor attaches to the housing and/or the drill bit with male/female connectors, quick connectors, screw threads, screw(s), hardware fixation, interlocking devices, or any combination thereof.

The attachment may be by hand and may result in the assembled state shown in FIG. 13. In another embodiment, the absolute orientation sensor is able to be detached and re-attached to the housing and/or the drill bit with the use of a separate tool. For example, in some embodiments a screw driver may be used to remove screws that attach the absolute orientation sensor to the housing. In an alternative embodiment, the absolute orientation sensor is permanently attached (e.g., by welding or overmolding) and cannot be detached from the rest of the instrument without at least partially damaging the instrument.

The absolute orientation sensor 1130 may be removed from the housing 1102 by hand. For example, the absolute orientation sensor 1130 can be slid backward from the protrusion by the user.

In an embodiment, the absolute orientation sensor is integrated into the housing or drill bit. For example, the housing may include a central cavity that is configured to receive the absolute orientation sensor and fixedly attach the absolute orientation sensor to the housing. The cavity may receive the entire absolute orientation sensor.

In some embodiments, any part of the sensor can be independently integrated in a tool body. For example, an electronic sensor component, display, and/or power source (or any combination thereof) may be attached to the tool body as needed to provide orientation.

In an embodiment, the absolute orientation sensor can function when separated from the housing. For example, the absolute orientation sensor may function as stand-alone "digital level" or gauge, functioning as a calibrator or digital level for any and all tools or equipment, including those that are manually powered with no electronic components. The free-standing "digital level" can provide the user absolute orientation coordinates to any instrument or object in a medical or surgical context. This may allow the orientation system to "calibrate" or "orient" in space a "manual" tool, instrument, or device that itself does not have electronic component. Additionally, the tool can mate via a formal paired connector, either physically or digitally, to operably couple or provide orientation information to a specific sensor.

In an embodiment, the absolute orientation sensor and the instrument it is associated with can function as a single unit, which can be disposable or reusable.

In an embodiment, the absolute orientation sensor is attachable to/detachable from or permanently integrated into another surgical/medical device/equipment. For example, the absolute orientation sensor may be attachable to/detachable from or permanently integrated into wearable devices (e.g., surgical gloves, surgical masks, headgear, and/or surgical eyewear), image acquisition machines, patient tables/beds, anesthesia monitoring equipment, and the like.

The absolute orientation sensor 1130 may include an accelerometer 135, a gyroscope 140, a magnetometer 145, a device processor 150, a power source 155, an input/output device 185, a communication link 190, and/or an audio device 195 (each shown in FIG. 2). For example, the absolute orientation sensor 1130 may include each component in a similar manner as the absolute orientation sensor 130 described with reference to FIG. 2 above.

The display portion may be similar to the display 870 described with reference to FIG. 9 above. For example, the display portion may display the current orientation of the absolute orientation sensor 1130.

Figure 15:
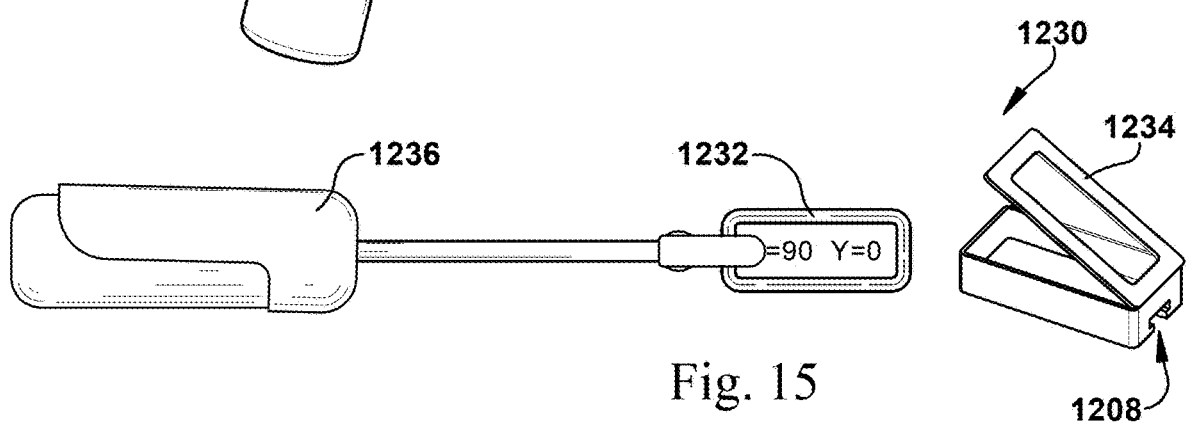
FIG. 15 is a front illustration of another embodiment of an absolute orientation sensor and an introducing tool configured to grip an absolute orientation sensor component and insert the absolute orientation sensor component into a sensor case of the absolute orientation sensor.
Figure 16:
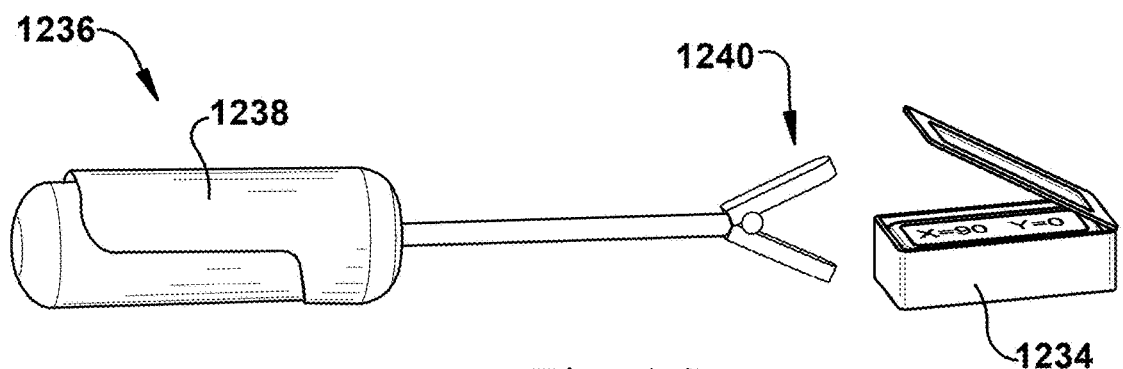
FIG. 16 is a front perspective illustration of the absolute orientation sensor and introducing tool of FIG. 15, the absolute orientation sensor being in an open position.
Figure 17:
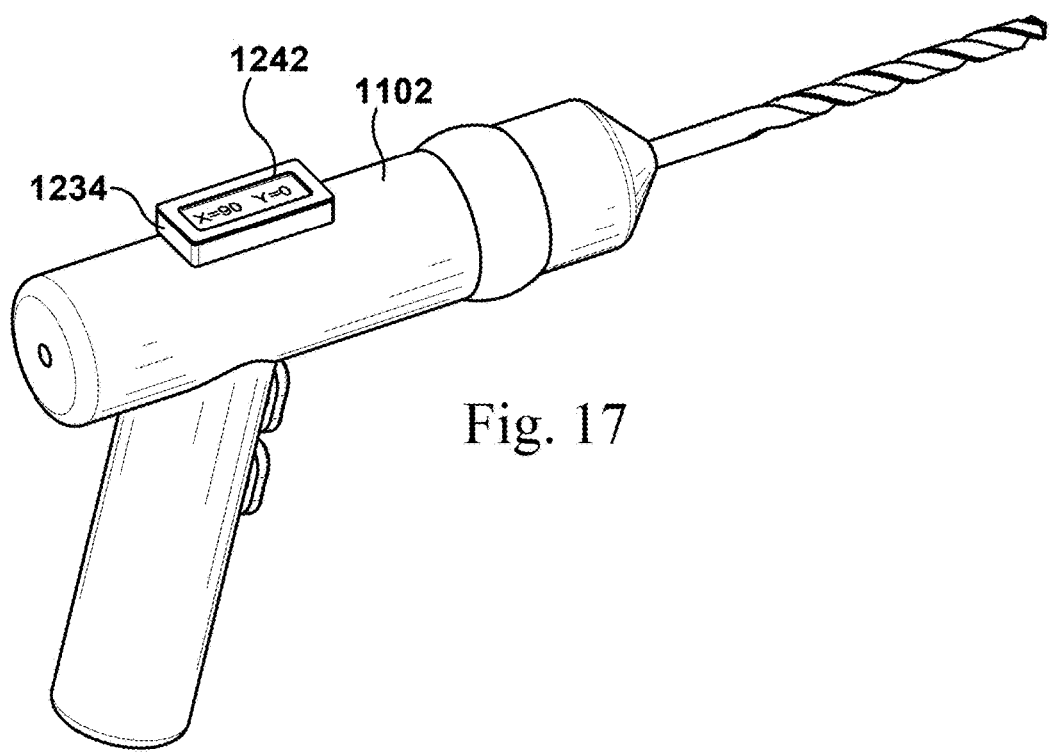
FIG. 17 is a front perspective illustration of another embodiment of a surgical instrument attached to the absolute orientation sensor of FIG. 16, the absolute orientation sensor being in a closed position.
Figure 18:
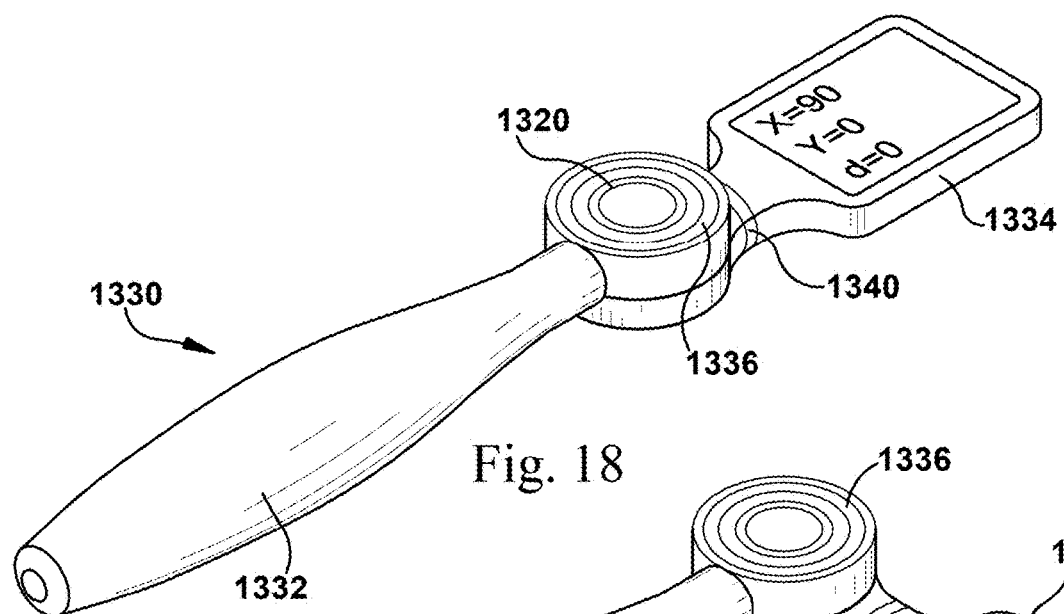
FIG. 18 is a front perspective illustration of another embodiment of an absolute orientation sensor that includes a handle and a movable display.
Figure 19:
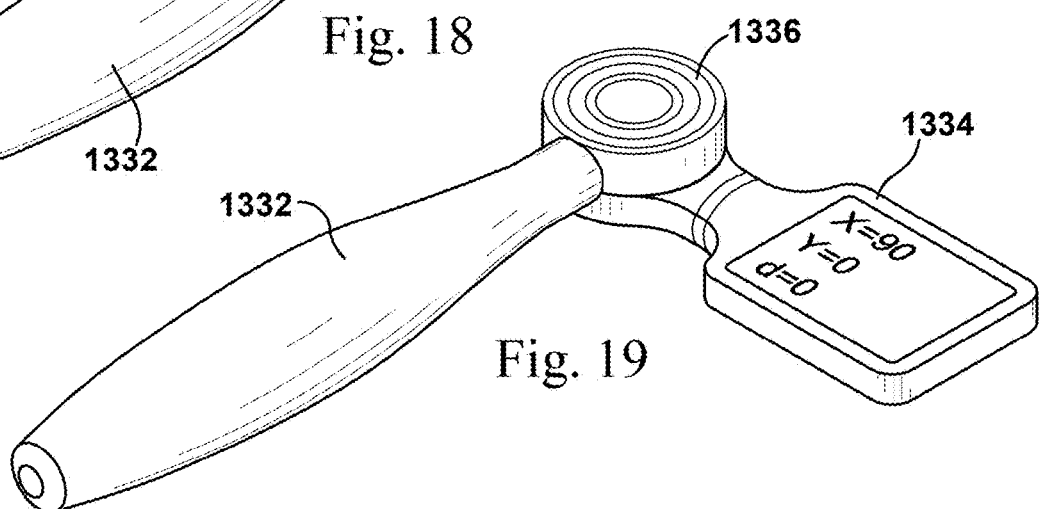
FIG. 19 is a front perspective illustration of the absolute orientation sensor of FIG. 18 with the display rotated relative to a handle.

Turning now to FIGS. 15-17, an exemplary embodiment of an absolute orientation sensor is shown at 1230. The absolute orientation sensor 1230 is substantially the same as the above-referenced absolute orientation sensor 1130, and consequently the same reference numerals but indexed by 1200 are used to denote structures corresponding to similar structures in the absolute orientation sensor 1230. In addition, the foregoing description of the absolute orientation sensor 1130 is equally applicable to the absolute orientation sensor 1230 except as noted below. Moreover, it will be appreciated that aspects of the absolute orientation sensors may be substituted for one another or used in conjunction with one another where applicable.

The absolute orientation sensor 1230 may include an absolute orientation sensor component 1232 and a sensor case 1234. The sensor case 1234 may be configured to receive the absolute orientation sensing component 1232 and at least partially fix the absolute orientation sensing component 1232 relative to the instrument body. For example, the sensor case 1234 may include a groove 1208 that is configured to attach to a protrusion of a surgical tool (e.g., attach to the surgical drill housing 1102).

The absolute orientation sensing component 1232 may include an accelerometer 135, a gyroscope 140, a magnetometer 145, a device processor 150, a power source 155, an input/output device 185, a communication link 190, and/or an audio device 195 (each shown in FIG. 2). For example, the absolute orientation sensing component 1232 may include each component in a similar manner as the absolute orientation sensor 130 described with reference to FIG. 2 above.

A user may use an introducing tool 1236 to move the absolute orientation sensing component 1232 into an interior of the sensor case 1234, as shown in FIG. 16. The introducing tool 1236 may have a handle 1238 configured to grip and release grippers 1240 that are able to hold and release the absolute orientation sensing component 1232. When the absolute orientation sensing component 1232 is entirely inside the interior of the sensor case 1234, the sensor case 1234 may be closed to hermetically seal the absolute orientation sensing component 1232 from the exterior environment.

The absolute orientation sensing component 1232 may include all or some of the electrical sensor components, including a display. For example, as shown in FIG. 17, the sensor case 1234 may include a window 1242 to allow a user to see a display of the absolute orientation sensing component 1232. The display may be similar to the display 870 described with reference to FIG. 9 above. For example, the display portion may display the current orientation of the absolute orientation sensor 1130.

The sensor case 1234 may attach to the housing 1102 via the groove 1208 in a similar manner to the absolute orientation sensing 1130 described above.

In an embodiment, the absolute orientation sensor includes feedthroughs from a nonsterile enclosure to a sterile external space, separating the electronics from the surgical/biological environment. For example, the absolute orientation sensor and its associated components can be nonsterile and contained within an externally sterile package that is introduced to the surgical field sterilely. More specifically, the nonsterile components can be introduced into the field inside of the package after the outside of the package has been sterilized.

In an embodiment, the absolute orientation sensor is integrated within a tool or instrument itself, with hermetic/sterile enclosures and "feed-throughs" that allow instrumentation and the like to "pass through" a housing that contains electronics and enter the sterile surgical/medical field. The orientation sensor, its power source, various input and output hardware, and the tool itself can be integrated into a single sealed enclosure which can then be entirely sterilized.

In an alternative embodiment, the orientation sensor and any combinations of its power source, input, output, displays, feedback, monitors, and any and all combinations can be separately sealed in a discrete sterile or sterilizable package and can mate with a working portion of a tool.

In another embodiment, the absolute orientation sensor is contained in a nonsterile environment that is introduced sterile or otherwise contained and cordoned from the sterile environment.

Turning now to FIGS. 18-22, an exemplary embodiment of an absolute orientation sensor is shown at 1330. The absolute orientation sensor 1330 is similar to the above-referenced absolute orientation sensor 130, and consequently the same reference numerals but indexed by 1300 are used to denote structures corresponding to similar structures in the absolute orientation sensor 1330. In addition, the foregoing description of the absolute orientation sensor 130 is equally applicable to the absolute orientation sensor 1330 except as noted below. Moreover, it will be appreciated that aspects of the absolute orientation sensors may be substituted for one another or used in conjunction with one another where applicable.

The absolute orientation sensor 1330 may include a handle 1332 a display arm 1334 that is rotatable about multiple axes. The handle 1332 may include electronical components including an absolute orientation sensing component (not shown). The handle 1332 may be attached to a rotation bearing 1320 that is configured to slide onto a tool and allows the handle 1332 to rotate about a longitudinal axis. An outer rotational bearing 1336 may connect the handle 1332 to the display arm 1334 such that the display arm 1334 is rotatable about the longitudinal axis, as exemplified in FIG. 19.

The display arm 1334 may include a display to allow a user to see an orientation of the handle 1332 and any tool attached to the handle 1332. The display arm 1334 may include a transverse rotation bearing 1340 that is configured to allow the display portion of the display arm 1334 to rotate about a lateral axis that is transverse to the longitudinal axis.

The transverse rotation bearing 1340 may include or be connected to a ratchet (not shown) that allows the display portion to rotate in only one direction and not in an opposite direction. In an embodiment, the outer rotation bearing also or alternatively includes or is attached to a ratchet to allow the display arm to rotate in only one direction and not the opposite direction.

The display portion may be similar to the display 870 described with reference to FIG. 9 above. For example, the display portion may display the current orientation of the absolute orientation sensor 1330.

Figure 20:
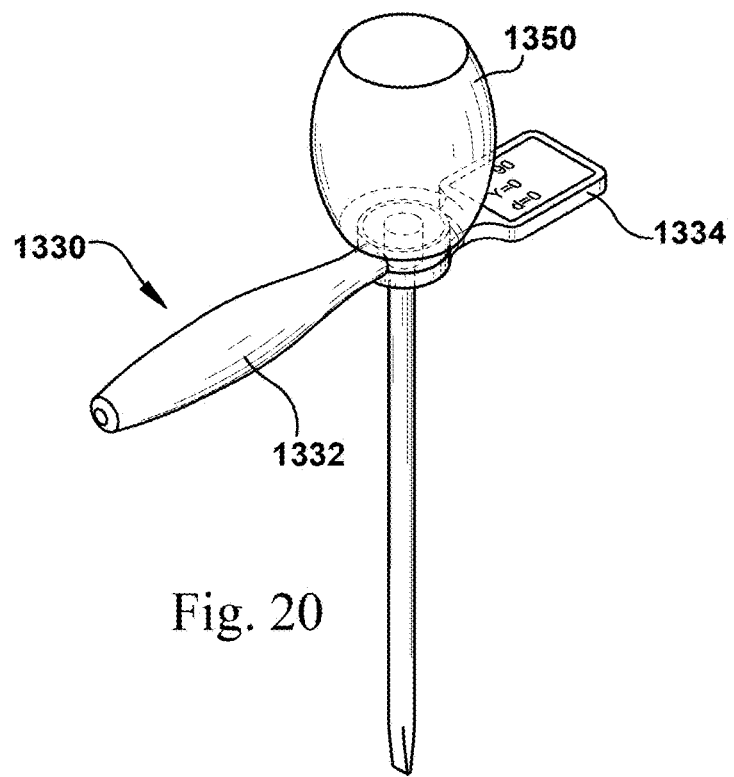
FIG. 20 is a front perspective illustration of the absolute orientation sensor of FIG. 18 in combination with an awl.

FIG. 20 illustrates the absolute orientation sensor 1330 in combination with an awl 1350. The shaft of the awl 1350 can be slide into the central hole of the rotation bearing 1320 until a handle of the awl 1350 abuts the absolute orientation sensor 1330.

The display portion can be oriented to be more easily viewed by a user by adjusting the display arm 1334 and the corresponding display portion relative to the longitudinal and lateral axes. For example, the user may hold the handle 1332 with one hand and use the other hand to adjust the display arm 1334 and display portion.

Figure 21:
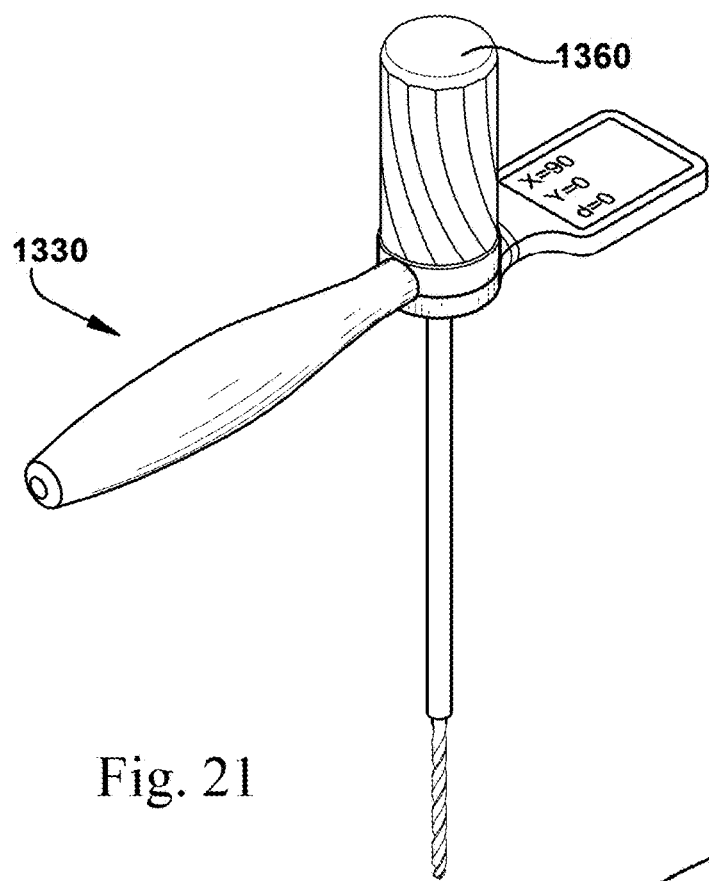
FIG. 21 is a front perspective illustration of the absolute orientation sensor of FIG. 20 in combination with a tap.
Figure 22:
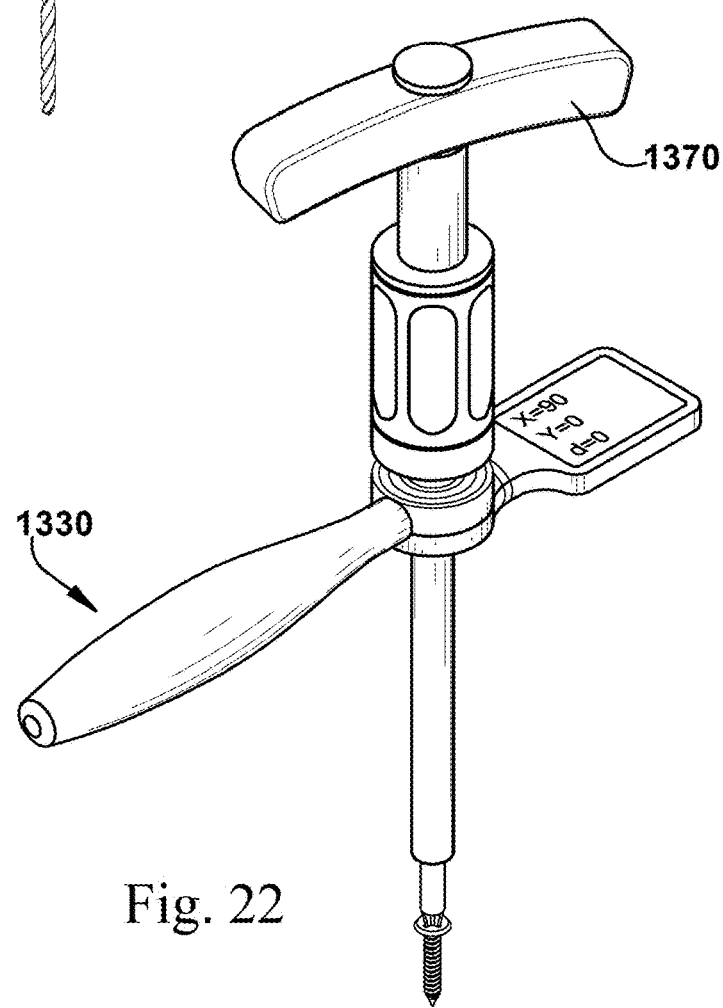
FIG. 22 is a front perspective illustration of the absolute orientation sensor of FIG. 21 in combination with a screwdriver.

FIGS. 21 and 22 illustrate the absolute orientation sensor 1330 in combination with a tap 1360 and a screw driver 1370, respectively. Each of the tap 1360 and the screw driver 1370 may be combined with the absolute orientation sensor 1330 in a similar manner as the awl 1350.

Figure 23:
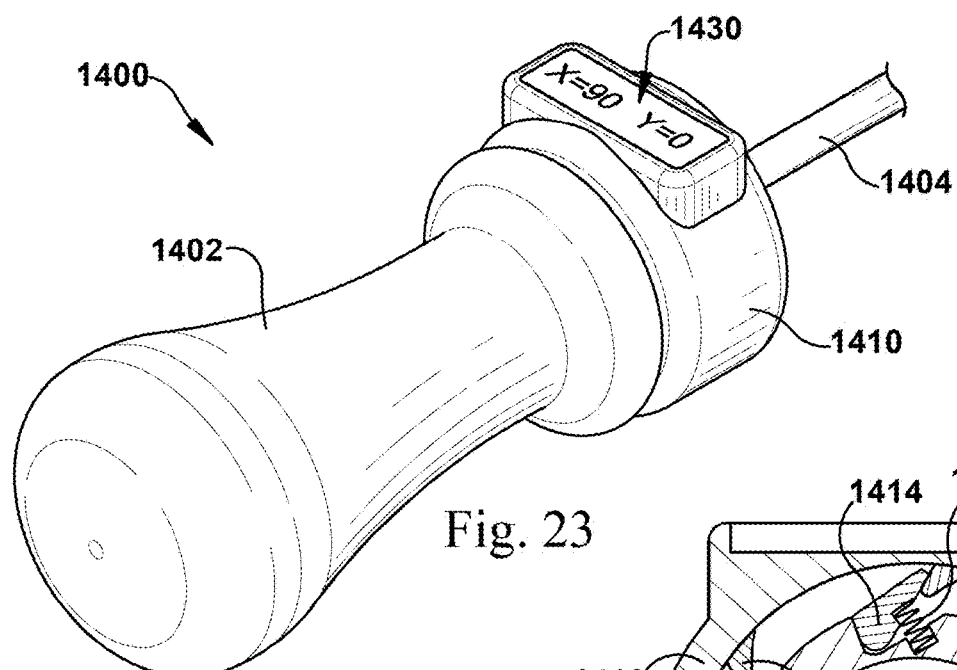
FIG. 23 is a front perspective illustration of another embodiment of a surgical instrument that is rotatably attached to another embodiment of an absolute orientation sensor.
Figure 24:
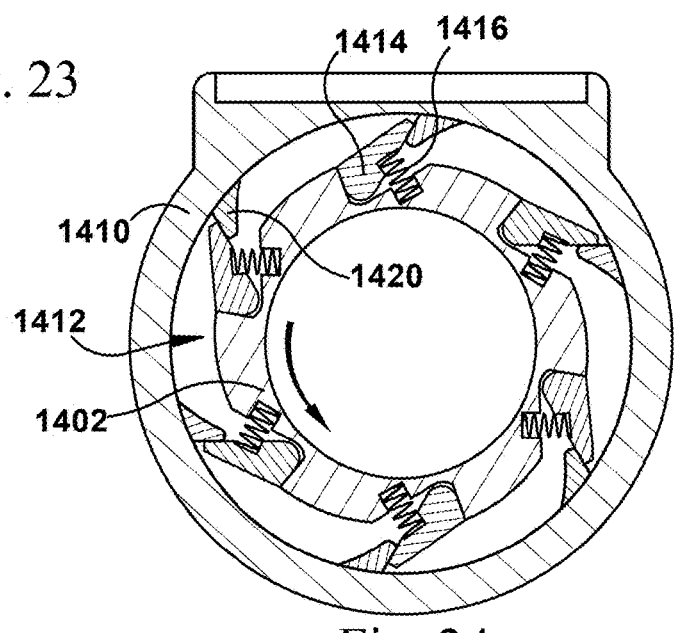
FIG. 24 is a front cross-sectional illustration of the absolute orientation sensor of FIG. 23 including a ratchet.

Turning now to FIGS. 23 and 24, an exemplary embodiment of a surgical screw driver is shown at 1400. The surgical screwdriver 1400 is similar to the above-referenced surgical drill 1100, and consequently the same reference numerals but indexed by 1400 are used to denote structures corresponding to similar structures in the surgical screw driver 1400. In addition, the foregoing description of components of the surgical drill 1100 is equally applicable to similar components of the surgical screw driver 1400 except as noted below. Moreover, it will be appreciated that aspects of the surgical screwdriver and the surgical drill may be substituted for one another or used in conjunction with one another where applicable.

The screw driver 1400 includes a handle 1402, a shaft 1404, and an absolute orientation sensor 1430 partially fixed relative to the handle 1402 and the shaft 1404. In an embodiment, the absolute orientation sensor is partially fixed relative to the only the shaft or only the handle.

The absolute orientation sensor 1430 includes a sleeve 1410 that is ratchetably coupled to the handle 1402 so that the absolute orientation sensor 1430 is able to rotate in only one direction about a longitudinal axis of the handle 1402 or the shaft 1404. For example, when a user is holding the handle 1402, the absolute orientation sensor 1430 can be rotated so that a display portion of the absolute orientation sensor 1430 is more easily viewable by the user. In an embodiment, an absolute orientation sensing element of the absolute orientation sensor is entirely fixed to the display portion. In another embodiment, the absolute orientation sensing element is partially fixed to the display portion.

FIG. 24 illustrates a cross-section of the screw driver 1400 through the absolute orientation sensor 1430. The screw driver 1400 includes ratchet 1412 that ratchetably couples the sleeve 1410 to the handle 1402.

The ratchet 1412 includes multiple fingers 1414 biased radially outward by springs 1416. The fingers 1414 are configured to allow the handle 1402 to rotate counter-clockwise (when viewing FIG. 24) but not clockwise. For example, when the handle 1402 is urged clockwise relative to the sleeve 1410, the fingers 1414 lock against corresponding protrusions 1420 that are fixed to the sleeve 1410. When the handle 1402 is rotated counter-clockwise relative to the sleeve 1410 and the fingers 1414 abut a protrusion 1420, the fingers 1414 move radially inward of the corresponding protrusion 1420 and compress the corresponding spring 1416.

When the handle 1402 is moved linearly, the absolute orientation sensor 1430 may move with the handle 1402. For example, the absolute orientation sensor 1430 may detect linear movement of the handle 1402 along any of three independent axes and/or may detect rotation of the handle 1402 about either of the two independent axes that are perpendicular to the longitudinal axis.

In another embodiment, the handle is coupled to the absolute orientation sensor by a sprocket-type mechanical linkage. In another embodiment, the handle is coupled to the absolute orientation sensor by another coupling or linkage. For example, a magnetic, electronic or chemical linkage may be configured to allow the absolute orientation sensor to be partially fixed relative to the tool.

In an embodiment, the absolute orientation sensor is coupled to a tool/device used in a medical/surgical context which allows independent motion of the sensor relative to the tool in certain planes. For instance, a ratchet allows the absolute orientation sensor to remain in a stable orientation while an instrument (or part of the instrument) that uses axial rotation for its function (for example, a screw driver or drill) can turn. This allows a constant read of the orientation of the instrument (e.g., screw driver) even while the instrument is moving in a specific plane/axis (spinning coaxially). Similarly, relative linear motion between the absolute orientation sensor and the corresponding tool can be implemented. For example, instruments that linearly move or include linearly moving components (e.g., nested components that move linearly or with a rotatory fashion with respect to one another) can be combined with an absolute orientation sensor that would not linearly move with such instruments or components. Such partial relative movement allows the absolute orientation sensor to remain in the same position relative to the user.

Figure 25:
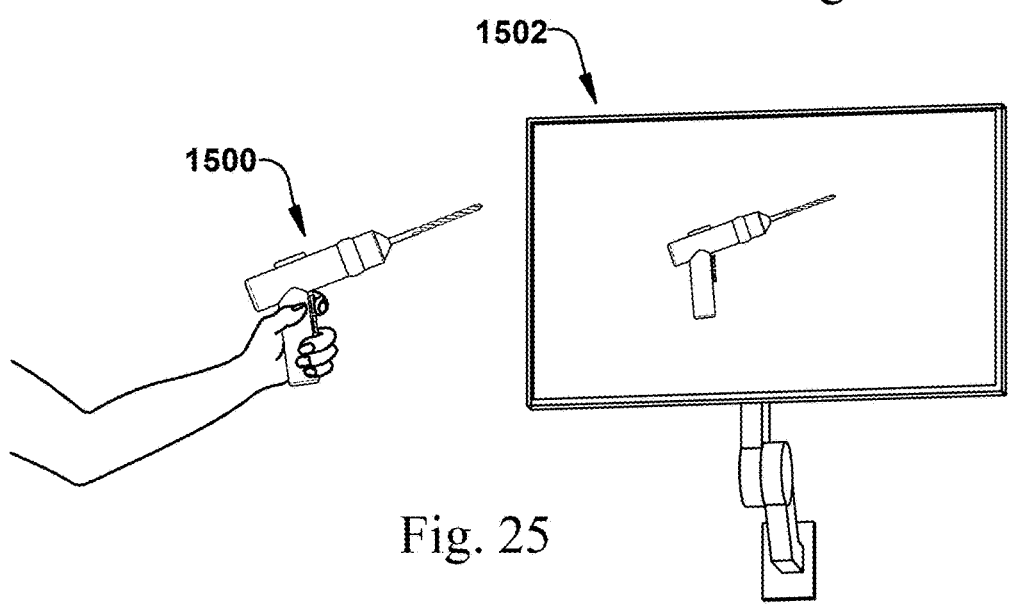
FIG. 25 is a front illustration of another embodiment of a surgical instrument and a display mimicking the orientation of the surgical instrument in real-time.

Turning now to FIG. 25, an exemplary embodiment of a surgical drill is shown at 1500. The surgical drill 1500 is substantially the same as the above-referenced surgical drill 1100, and consequently the same reference numerals but indexed by 1500 are used to denote structures corresponding to similar structures in the surgical drill 1500. In addition, the foregoing description of the surgical drill 1100 is equally applicable to the surgical drill 1500 except as noted below. Moreover, it will be appreciated that aspects of the surgical drills may be substituted for one another or used in conjunction with one another where applicable.

The orientation information detecting movement of the surgical drill 1500 may be transmitted to a display 1502 so that movement of the surgical drill 1500 can be mimicked on the display 1502. The display 1502 allows a user to see a virtual representation of the movement and absolute orientation of the surgical drill 1500. In an embodiment, the display may provide a virtual representation of a patient or other objects in addition to a virtual representation of the surgical drill to provide the user with a visualization of the surgical drill. The visualization may not be otherwise available to the user do to the user's position or location.

In an embodiment, captured angle, position, velocity, and acceleration data reproduced in the virtual representation of the tool displayed on a monitor.

Figure 26:
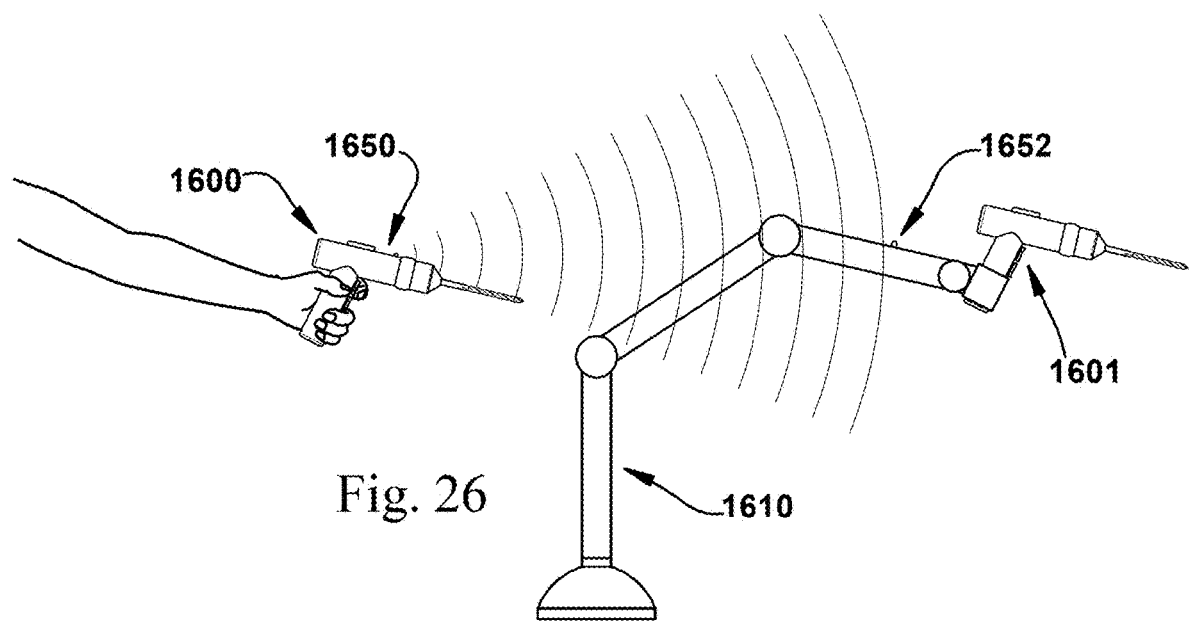
FIG. 26 is a front illustration of another embodiment of a surgical instrument and a robotic arm configured to mimic the orientation of the surgical instrument in real-time.

Turning now to FIG. 26, an exemplary embodiment of a surgical drill is shown at 1600. The surgical drill 1600 is substantially the same as the above-referenced surgical drill 1500, and consequently the same reference numerals but indexed by 1600 are used to denote structures corresponding to similar structures in the surgical drill 1600. In addition, the foregoing description of the surgical drill 1500 is equally applicable to the surgical drill 1600 except as noted below. Moreover, it will be appreciated that aspects of the surgical drills may be substituted for one another or used in conjunction with one another where applicable.

The surgical drill 1600 may communicate its orientation to a robotic arm 1610. The robotic arm 1610 may control a second surgical drill 1601 based on the orientation of the surgical drill 1600. For example, the robotic arm 1610 may move the surgical drill 1601 in the same manner that the surgical drill 1600 is moved by a user.

The surgical drill 1601 may be identical to the surgical drill 1600. In an embodiment, the surgical drill controlled by the arm does not include an orientation sensor.

The surgical drill may include a wireless transmitter 1650 that wirelessly communicates with a wireless receiver 1652 of the robotic arm 1610. For example, when the surgical drill 1600 is moved, the transmitter 1650 may communicate such movement to the receiver 1652 so that the robotic arm 1610 can mimic such movement with the surgical drill 1601. Mimicking movement allows a user to remain in an unsterile environment while operating the robotic arm 1610, which may be in a sterile environment with a patient.

Figure 27:
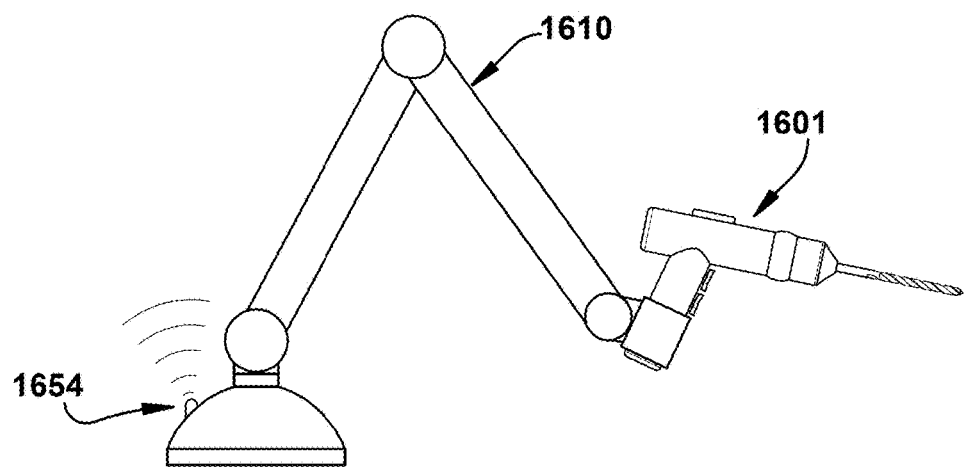
FIG. 27 is a front illustration of another embodiment of a robotic arm that is configured to transmit the orientation feedback of a surgical instrument and configured to receive a target orientation.

As shown in FIG. 27, the robotic arm 1610 may include a transmitter 1654 to provide feedback orientation information pertaining to the surgical drill 1601. The feedback may be utilized by a processor built into the surgical drill 1600 or a separate processor to refine the orientation information provided to the robotic arm 1610 and/or to refine movement of the robotic arm 1610.

Figure 28:
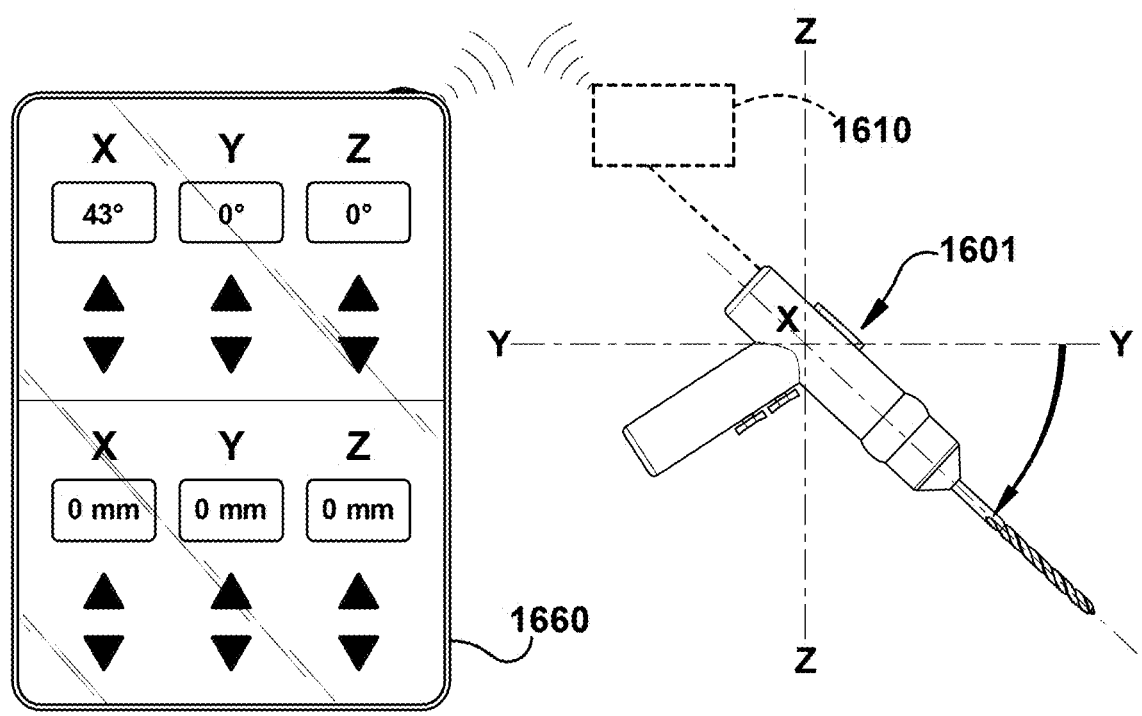
FIG. 28 is a front illustration of the surgical instrument of FIG. 27 in combination with an orientation input configured to send a target orientation to a receiver operably coupled to the surgical instrument.

Referring now to FIG. 28, an orientation controller 1660 may communication an orientation to the robotic arm 1610 (schematically shown in FIG. 28) and the robotic arm 1610 may move the surgical drill 1601 to that orientation. For example, a user may use input buttons on the orientation controller 1660 to set orientation angles and positions. The orientation controller 1660 may wirelessly communication the set orientation to the robotic arm 1610 and the robotic arm may move the surgical drill 1601 to the set orientation.

In an embodiment, the robotic arm includes one or more stepper motor to determine the orientation of the surgical drill held by the robotic arm in addition to the orientation sensor of the surgical drill held by the robotic arm. In another embodiment, the position of the surgical drill held by the robotic arm is determined entirely by sensors or stepper motors of the robotic arm.

Figure 29:
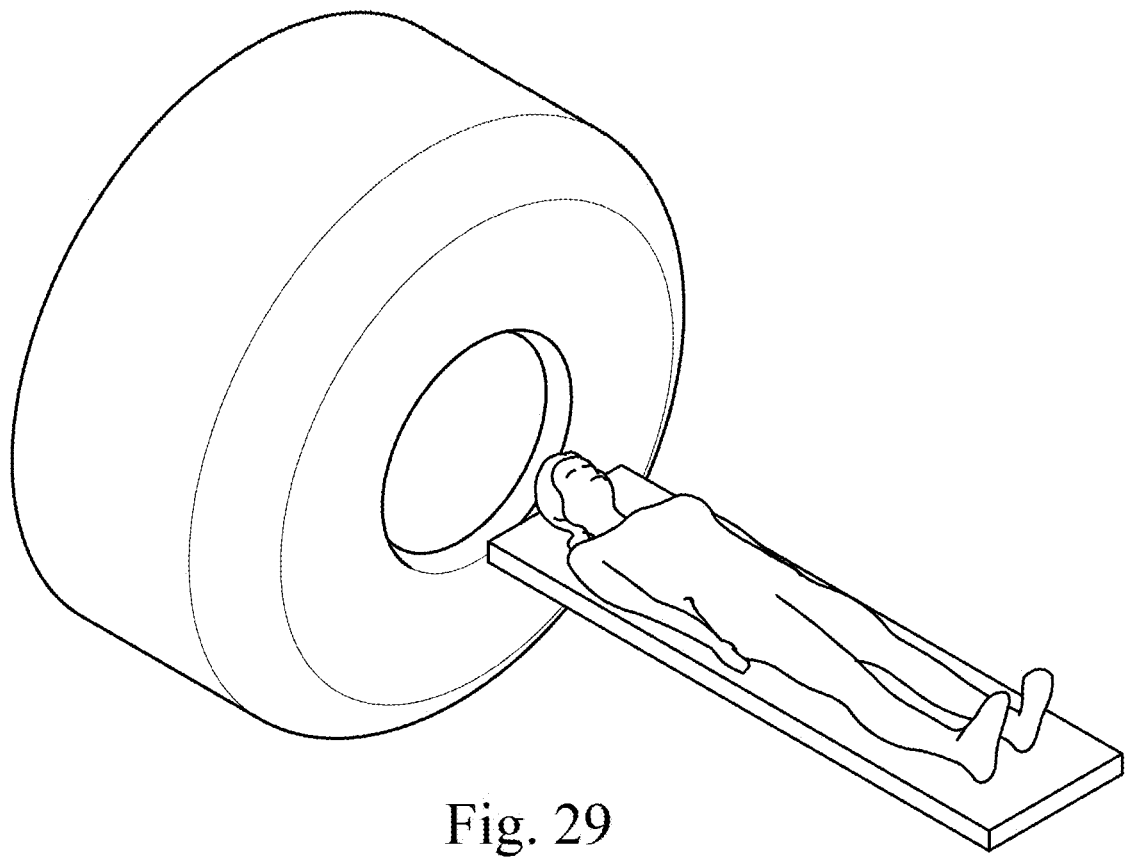
FIG. 29 is a front perspective illustration of a patient entering a computed tomography (CT) scanner.

Turning now to FIG. 29, a computed tomography (CT) scanner may be used to identify an area of interest of a patient. For example, the patient's pelvic region may be an area of interest and a CT image of a cross-section of the patient's pelvic region may include a desired location to be biopsied.

Figure 30:
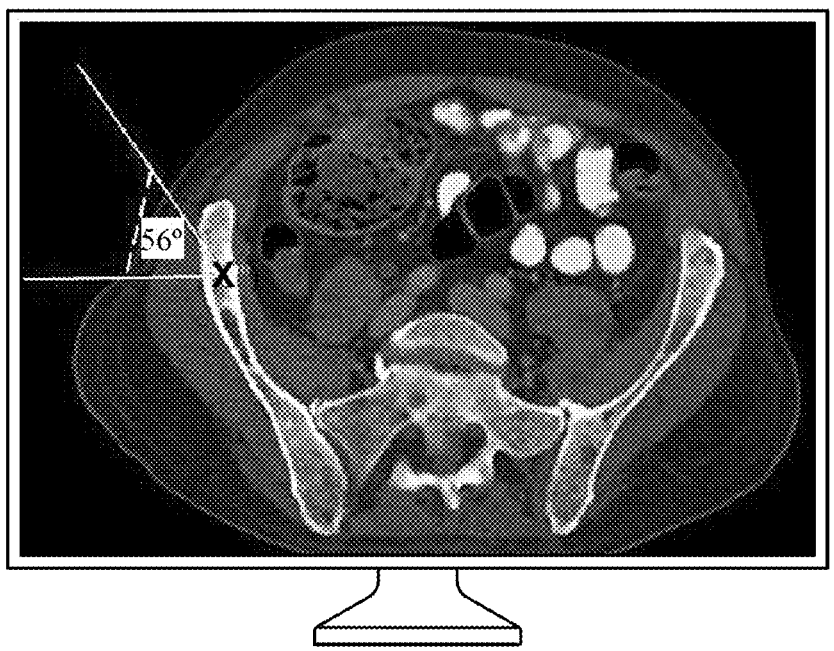
FIG. 30 is a front illustration of a display showing a CT scan of the patient of FIG. 29 and a target entry point and orientation for a biopsy needle.
Figure 31:
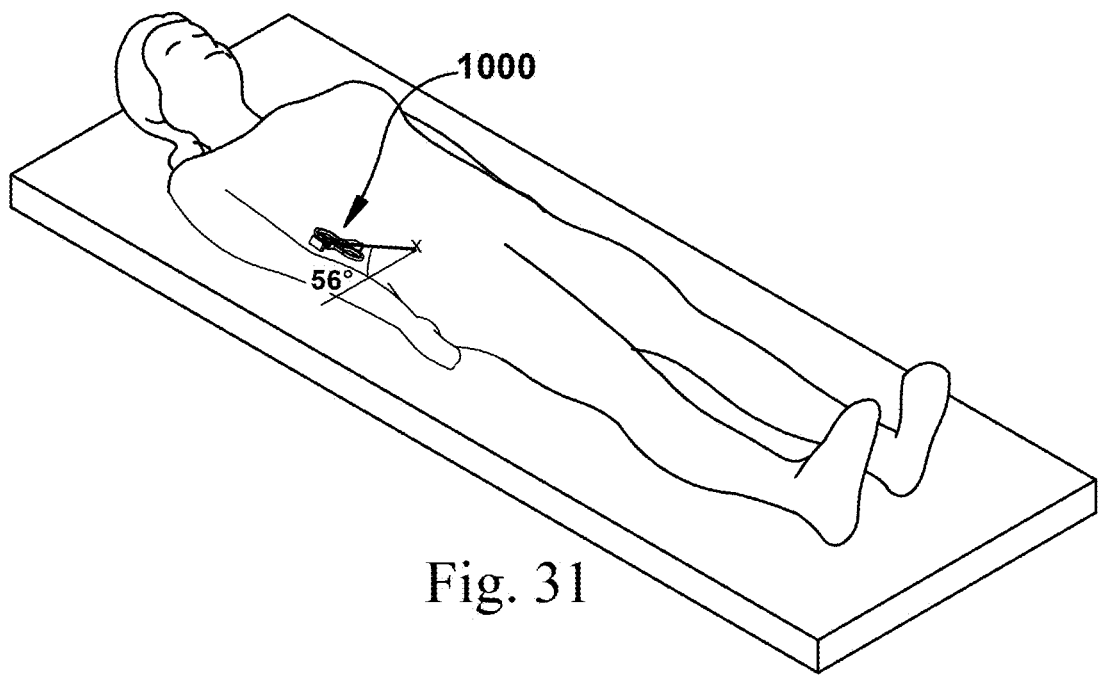
FIG. 31 is a front perspective illustration of the patient of FIG. 29 and the biopsy needle of FIG. 11.

FIG. 30 illustrates an example of a CT image in which a location to be biopsied X is shown along with a desired entry angle of a biopsy needle. A point of entry in the patient may be determined based on the location to be biopsied X and the entry angle. A doctor may determine any or all of the location to be biopsied X, the entry angle, and/or the point of entry.

The biopsy needle 1000, discussed above, or another tool discussed above, may be inserted into the patient at the point of entry to reach the location to be biopsied X. Orientation feedback from the biopsy needle 1000 may allow the user to insert the biopsy needle into the patient and reach the location to be biopsied X at the desired entry angle and via the desired point of entry, without necessitating a second CT scan. For example, the biopsy needle 1000 may provide feedback to the user based on the desired entry angle, point of entry, and/or location to be biopsied X so that the user is informed regarding when the orientation of the biopsy needle 1000 is correct or incorrect.

In an embodiment, the biopsy needle provides feedback to the user (e.g., with lights, sound, or with another feedback component/functionality discussed above) to alert the user that the orientation is correct and/or incorrect. For example, the biopsy needle may include lights configured to display a particular pattern or color when the orientation of the biopsy needle is correct (e.g., within a predetermined threshold of the desired orientation). The biopsy needle may also or alternatively be configured to display a different pattern or color when the orientation of the biopsy needle is incorrect (e.g., outside of a predetermined threshold of the desired orientation). In some embodiments, the current orientation of the biopsy needle may be displayed in an overlaid fashion with the desired orientation.

The biopsy needle 1000 with its absolute orientation sensor 1030 (labeled in FIG. 11) can be used in conjunction with conventional imaging intra-operatively. For example, the absolute orientation sensor may be used in interventional radiology. With the use of a biopsy needle with orientation sensing, a physician can position the instrument at a known anatomic landmark or over area of interest; using any imaging modality employed by the interventional radiologists, such as fluoroscopy, CT scanning, ultrasound, MRI, and the like, the tool can be repositioned based on measurements made after additional imaging has been obtained. This allows the biopsy needle 1000 to be introduced and/or advanced in a guided fashion into the desired area of the patient's body.

In an embodiment, a robotic arm is configured to insert the biopsy needle based on the desired area of the patient's body. For example, the desired entry angle, location of interest, and/or orientation are input to the robotic arm and the robotic arm inserts the biopsy needle based on the designated inputs.

According to one aspect of the invention, a surgical instrument comprises an instrument body, an absolute orientation sensor including an absolute orientation sensing component, the absolute orientation sensor being configured to be attached to the instrument body such that when the absolute orientation sensor is attached to the instrument body the absolute orientation sensing component would be at least partially fixed relative to the instrument body. When the absolute orientation sensing component is at least partially fixed relative to the instrument body the absolute orientation sensing component would be operable to detect a plurality of orientation data associated with at least one orientation condition of the surgical instrument relative to the Earth's magnetic field without requiring calibration by a separate arbitrary reference plane, the absolute orientation sensor being at least partially detachable from the instrument body such that the absolute orientation sensing component is removable from the instrument body, where when the absolute orientation sensing component is removed the absolute orientation sensing component would not be operable to detect the plurality of orientation data associated with the at least one orientation condition of the surgical instrument.

The absolute orientation sensing component may be configured to be removable from the instrument body by hand.

The absolute orientation sensor may be configured to slide onto and off of the instrument body such that the absolute orientation sensing component is removable from the instrument body.

The absolute orientation sensor may include a sleeve that is configured to slide onto and off of a shaft of the instrument body such that the absolute orientation sensing component is removable from the instrument body.

The absolute orientation sensor may include a sensor case that is configured to receive the absolute orientation sensing component and at least partially fix the absolute orientation sensing component relative to the instrument body.

The sensor case may have an open position and a closed position, and when the sensor case is in the closed position an interior of the sensor case is hermetically sealed from the atmosphere, and when the sensor case is in the open position the interior is configured to receive the absolute orientation sensing component such that the absolute orientation sensing component can be retained within the interior when the sensor case is in the closed position.

The surgical instrument may include a device processor operable for controlling one or more components of the surgical instrument.

The absolute orientation sensor may be operatively coupled to the device processor and controlled in part by the device processor, the absolute orientation sensing component may comprise an accelerometer, gyroscope, and magnetometer, wherein the absolute orientation sensing component is operable to generate a plurality of orientation status data on at least a portion of the plurality of detected orientation data.

The surgical instrument may further include at least one power source operatively coupled to the absolute orientation sensing component, wherein the at least one power source is operable to generate a supply of power for operation of the device processor and the absolute orientation sensing component.

The surgical instrument may be in combination with a hermetically sealed enclosure, and the surgical instrument may be enclosed within the hermetically sealed enclosure.

According to another aspect of the invention, a surgical instrument comprises an instrument body, an absolute orientation sensor including an absolute orientation sensing component, the absolute orientation sensor being configured to be attached to the instrument body such that when the absolute orientation sensor is attached to the instrument body the absolute orientation sensing component would be partially fixed relative to the instrument body. When the absolute orientation sensing component is at least partially fixed relative to the instrument body the absolute orientation sensing component would be operable to detect a plurality of orientation data associated with at least one orientation condition of the surgical instrument relative to the Earth's magnetic field without requiring calibration by a separate arbitrary reference plane, the absolute orientation sensor being configured to partially isolate movement of the instrument body from absolute orientation sensing component when the absolute orientation sensor is attached to the instrument body, where when the absolute orientation sensing component is partially fixed relative to the instrument body the instrument body would be partially movable relative to the absolute orientation sensing component.

The instrument body may be rotatable relative to the absolute orientation sensing component when the absolute orientation sensor is attached to the instrument body.

The absolute orientation sensor may include a ratchet that is configured to allow the instrument body to move relative to the absolute orientation sensing component in a first direction and configured to not allow the absolute orientation sensor component to move in a second direction opposite the first direction.

The absolute orientation sensor may include a ratchet that is configured to allow the instrument body to rotate relative to the absolute orientation sensing component in the first direction and configured to not allow the absolute orientation sensor component to move in the second direction.

The surgical instrument may further comprise a display operatively coupled to the device processor, the display being operable to display at least a portion of the plurality of generated orientation status data thereon, and the display may be configured to be partially fixed relative to the instrument body, where when the display is partially fixed relative to the instrument body the instrument body would be partially movable relative to the display.

According to another aspect of the invention, a surgical instrument comprises a device processor operable for controlling one or more components of the surgical instrument, at least one light source operatively coupled to the device processor and controlled in part by the device processor, the device processor being configured to operate the light source based on the orientation of the surgical instrument.

The device processor may be configured to activate one or more light sources of the at least one light source based on the orientation of the surgical instrument relative to a predetermined orientation.

The device processor may be configured to activate one or more light sources of the at least one light source when the surgical instrumented is oriented in a predetermined orientation.

The predetermined orientation may be within a predetermined threshold of a reference orientation.

The device processor may be configured to change the color of the light output by the at least one light source based on the orientation of the surgical instrument relative to a predetermined orientation.

The device processor may be configured to operate the least one light source based on the orientation of the surgical instrument relative to a predetermined orientation relative to a patient.

As mentioned above, features of any of the above aspects may be combined with one another. For example, a surgical instrument may include a detachable absolute orientation sensor that is partially fixable relative to an instrument body and the surgical instrument may provide feedback (e.g., light feedback) based on the orientation sensed by the absolute orientation sensor.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A surgical instrument comprising:
    an instrument body; and
    an absolute orientation sensor including an absolute orientation sensing component, wherein the absolute orientation sensor is configured to be attached to the instrument body such that when the absolute orientation sensor is attached to the instrument body the absolute orientation sensing component would be partially fixed relative to the instrument body, and wherein when the absolute orientation sensing component is at least partially fixed relative to the instrument body the absolute orientation sensing component would be operable to detect a plurality of orientation data associated with at least one orientation condition of the surgical instrument relative to the Earth's magnetic field without requiring calibration by a separate arbitrary reference plane;
    wherein the absolute orientation sensor is configured to partially isolate movement of the instrument body from absolute orientation sensing component when the absolute orientation sensor is attached to the instrument body, whereby when the absolute orientation sensing component is partially fixed relative to the instrument body the instrument body would be partially movable relative to the absolute orientation sensing component; and
    wherein the absolute orientation sensor includes a ratchet that is configured to allow the instrument body to move relative to the absolute orientation sensing component in a first direction and configured to not allow the instrument body to move relative to the absolute orientation sensing component in a second direction opposite the first direction, and wherein the absolute orientation sensor is concentric with the ratchet.

2. The surgical instrument of claim 1, wherein the instrument body is rotatable relative to the absolute orientation sensing component when the absolute orientation sensor is attached to the instrument body.

3. The surgical instrument of claim 1, wherein the ratchet is configured to allow the instrument body to rotate relative to the absolute orientation sensing component in the first direction and configured to not allow the instrument body to rotate relative to the absolute orientation sensing component in the second direction.

4. The surgical instrument of claim 1, further comprising:
    a display operatively coupled to a device processor of the surgical instrument, wherein the display is operable to display at least a portion of a plurality of orientation status data, that the absolute orientation sensing component is configured to generate, thereon, and wherein the display is configured to be partially fixed relative to the instrument body, whereby when the display is partially fixed relative to the instrument body the instrument body would be partially movable relative to the display.

5. The surgical instrument of claim 1, further including a handle for a user to hold.

6. The surgical instrument of claim 1, further including a display that is operatively coupled to a device processor, of the surgical instrument, and entirely fixed relative to the absolute orientation sensing component.

7. The surgical instrument of claim 6, wherein the display is rotatable with the absolute orientation sensing component about at least one axis relative to the instrument body.

8. The surgical instrument of claim 1, wherein the absolute orientation sensor further includes a rigid guide that is configured to slide and/or rotate about a shaft of the instrument body.

9. The surgical instrument of claim 8, wherein the rigid guide is formed by a rotational bearing.

10. The surgical instrument of claim 1, wherein a distal portion of the instrument body extends distally of the ratchet and the entire absolute orientation sensor and a proximal portion of the instrument body extends proximally of the ratchet and the entire absolute orientation sensor.

11. The surgical instrument of claim 1, wherein the instrument body includes a handle for a user to hold, wherein the handle extends proximally of the ratchet and the absolute orientation sensor.

12. The surgical instrument of claim 11, wherein the instrument body includes a shaft extending distally of the handle, the ratchet, and the absolute orientation sensor.

13. The surgical instrument of claim 12, wherein the handle and the shaft are configured to rotate in the first direction relative to the absolute orientation sensing component.

14. The surgical instrument of claim 13, wherein the absolute orientation sensor includes a display that is operatively coupled to a device processor, of the surgical instrument, and fixed relative to the absolute orientation sensing component.

15. The surgical instrument of claim 1, wherein the absolute orientation sensor further includes:
   a display that is operatively coupled to a device processor, of the surgical instrument, and entirely fixed relative to the absolute orientation sensing component; and
   a sleeve that is entirely fixed relative to the display and the absolute orientation sensing component, whereby the instrument body is configured to rotate in the first direction relative to the sleeve and the display, and the instrument body is configured to not rotate in the second direction relative to the sleeve and the display.

16. A surgical instrument comprising:
   an instrument body; and
   an absolute orientation sensor including an absolute orientation sensing component, wherein the absolute orientation sensor is configured to be attached to the instrument body such that when the absolute orientation sensor is attached to the instrument body the absolute orientation sensing component would be partially fixed relative to the instrument body, and wherein when the absolute orientation sensing component is at least partially fixed relative to the instrument body the absolute orientation sensing component would be operable to detect a plurality of orientation data associated with at least one orientation condition of the surgical instrument relative to the Earth's magnetic field without requiring calibration by a separate arbitrary reference plane;
   wherein the absolute orientation sensor is configured to partially isolate movement of the instrument body from absolute orientation sensing component when the absolute orientation sensor is attached to the instrument body, whereby when the absolute orientation sensing component is partially fixed relative to the instrument body the instrument body would be partially movable relative to the absolute orientation sensing component; and
   wherein the absolute orientation sensor includes a ratchet that is configured to allow the instrument body to move relative to the absolute orientation sensing component in a first direction and configured to not allow the instrument body to move relative to the absolute orientation sensing component in a second direction opposite the first direction,
   wherein the instrument body includes a handle for a user to hold, wherein the handle extends proximally of the ratchet and the absolute orientation sensor,
   wherein the instrument body includes a shaft extending distally of the handle, the ratchet, and the absolute orientation sensor, wherein the handle and the shaft are configured to rotate in the first direction relative to the absolute orientation sensing component,
   wherein the absolute orientation sensor includes a display that is operatively coupled to a device processor, of the surgical instrument, and fixed relative to the absolute orientation sensing component, and wherein the absolute orientation sensor includes a sleeve that is fixed relative to the display and the absolute orientation sensing component, whereby the handle and the shaft are configured to rotate in the first direction relative to the sleeve and the display, and the handle is not configured to rotate in the second direction relative to the sleeve and the display.

17. The surgical instrument of claim 16, wherein the absolute orientation sensor is concentric with the ratchet.

18. A surgical instrument comprising:
   an instrument body; and
   an absolute orientation sensor including an absolute orientation sensing component, wherein the absolute orientation sensor is configured to be attached to the instrument body such that when the absolute orientation sensor is attached to the instrument body the absolute orientation sensing component would be partially fixed relative to the instrument body, and
   wherein when the absolute orientation sensing component is at least partially fixed relative to the instrument body the absolute orientation sensing component would be operable to detect a plurality of orientation data associated with at least one orientation condition of the surgical instrument relative to the Earth's magnetic field without requiring calibration by a separate arbitrary reference plane;
   wherein the absolute orientation sensor is configured to partially isolate movement of the instrument body from absolute orientation sensing component when the absolute orientation sensor is attached to the instrument body, whereby when the absolute orientation sensing component is partially fixed relative to the instrument body the instrument body would be partially movable relative to the absolute orientation sensing component; and
   wherein the absolute orientation sensing component includes a ratchet that is configured to allow the instrument body to move relative to the absolute orientation sensing component in a first direction and configured to not allow the instrument body to move relative to the absolute orientation sensing component in a second direction opposite the first direction, and wherein the absolute orientation sensor includes a sleeve that is fixed relative to the absolute orientation sensing component and concentric with the ratchet.

* * * * *